United States Patent
Kam et al.

(10) Patent No.: US 11,839,415 B2
(45) Date of Patent: Dec. 12, 2023

(54) EXTENDED TAB SYSTEMS FOR REDUCING SPINAL RODS

(71) Applicant: K2M, Inc., Leesburg, VA (US)

(72) Inventors: Andrew Kam, Westmead (AU); Jens Richolt, Kronberg (DE); Daniel Genovese, Great Falls, VA (US); Josh Rubin, Paducah, KY (US); Geneva Goldwood, Tacoma, WA (US); Gordon Duncan Charles Dandie, Pymble (AU)

(73) Assignee: K2M, Inc., Leesburg, VA (US)

( * ) Notice: Subject to any disclaimer, the term of this patent is extended or adjusted under 35 U.S.C. 154(b) by 747 days.

(21) Appl. No.: 16/909,266

(22) Filed: Jun. 23, 2020

(65) Prior Publication Data

US 2020/0390480 A1 Dec. 17, 2020

Related U.S. Application Data

(63) Continuation of application No. 15/752,142, filed as application No. PCT/US2016/046523 on Aug. 11, 2016, now Pat. No. 10,702,317.

(60) Provisional application No. 62/204,553, filed on Aug. 13, 2015.

(51) Int. Cl.
  *A61B 17/70* (2006.01)
  *A61B 17/88* (2006.01)
  *A61B 90/00* (2016.01)

(52) U.S. Cl.
  CPC ........ *A61B 17/7088* (2013.01); *A61B 17/708* (2013.01); *A61B 17/7032* (2013.01); *A61B 17/7086* (2013.01); *A61B 17/7091* (2013.01); *A61B 17/8863* (2013.01); *A61B 2090/037* (2016.02)

(58) Field of Classification Search
  CPC ............ A61B 17/7079; A61B 17/7076; A61B 17/7077; A61B 17/708
  See application file for complete search history.

(56) References Cited

U.S. PATENT DOCUMENTS

| 6,740,086 B2 | 5/2004 | Richelsoph |
| 6,740,089 B2 | 5/2004 | Haider |
| 7,186,255 B2 | 3/2007 | Baynham et al. |
| 7,261,714 B2 | 8/2007 | Richelsoph |
| 7,717,942 B2 | 5/2010 | Schumacher |
| 7,811,288 B2 * | 10/2010 | Jones ................. A61B 17/7011 606/279 |

(Continued)

FOREIGN PATENT DOCUMENTS

| FR | 2988582 A1 | 10/2013 |
| WO | 2014196531 A1 | 12/2014 |

OTHER PUBLICATIONS

European Search Report issued in European Appln. No. 17210841.7 dated May 30, 2018.

(Continued)

*Primary Examiner* — Ellen C Hammond
(74) *Attorney, Agent, or Firm* — Lerner David LLP

(57) ABSTRACT

A rod reducer assembly is provided. The rod reducer includes a pedicle screw housing defining a rod-receiving passage therethrough. A tab is removably coupled to the pedicle screw housing by a frangible member. An extension is secured to the tab. The extension and the tab are separable from the pedicle screw housing upon application of a threshold force to the frangible member.

20 Claims, 28 Drawing Sheets

(56) References Cited

U.S. PATENT DOCUMENTS

| | | | |
|---|---|---|---|
| 7,842,073 B2 | 11/2010 | Richelsoph et al. | |
| 7,846,093 B2 | 12/2010 | Gorek et al. | |
| 7,927,360 B2 | 4/2011 | Pond, Jr. et al. | |
| 7,955,363 B2 | 6/2011 | Richelsoph | |
| 7,967,821 B2 | 6/2011 | Sicvol et al. | |
| 8,075,599 B2 | 12/2011 | Johnson et al. | |
| 8,221,471 B2 | 7/2012 | Kovach et al. | |
| 8,236,032 B2 | 8/2012 | Ramsay et al. | |
| 8,246,538 B2 | 8/2012 | Gorek | |
| 8,262,662 B2 | 9/2012 | Beardsley et al. | |
| 8,298,138 B2 | 10/2012 | Gorek et al. | |
| 8,376,940 B2 | 2/2013 | Gorek | |
| 8,388,659 B1 | 3/2013 | Lab et al. | |
| 8,409,255 B2 | 4/2013 | Richelsoph | |
| 8,523,913 B2 | 9/2013 | Jackson | |
| 8,663,292 B2 | 3/2014 | Dec et al. | |
| 8,685,029 B2 | 4/2014 | Dziedzic et al. | |
| 8,709,015 B2 | 4/2014 | Kolb et al. | |
| 8,734,338 B2 | 5/2014 | Gorek et al. | |
| 8,814,913 B2 | 8/2014 | Jackson | |
| 8,821,506 B2 | 9/2014 | Mitchell | |
| 8,852,239 B2 | 10/2014 | Jackson et al. | |
| 8,858,605 B1 | 10/2014 | Glatzer et al. | |
| 8,870,928 B2 | 10/2014 | Jackson | |
| 8,876,868 B2 | 11/2014 | Jackson | |
| 8,882,817 B2 | 11/2014 | Jones et al. | |
| 8,894,655 B2 | 11/2014 | Fallin et al. | |
| 8,932,210 B2 | 1/2015 | Woods | |
| 8,956,361 B2 | 2/2015 | Davenport et al. | |
| 8,979,851 B2 | 3/2015 | Fallin et al. | |
| 8,998,958 B2 | 4/2015 | Dauster et al. | |
| 9,050,141 B2 | 6/2015 | Zhang et al. | |
| 2008/0015601 A1 | 1/2008 | Castro et al. | |
| 2009/0149892 A1* | 6/2009 | Stad | A61B 17/7077 606/86 A |
| 2010/0036443 A1* | 2/2010 | Hutton | A61B 17/7082 606/86 R |
| 2011/0040335 A1 | 2/2011 | Stihl et al. | |
| 2011/0172715 A1 | 7/2011 | Pond, Jr. et al. | |
| 2011/0178560 A1 | 7/2011 | Butler et al. | |
| 2011/0257690 A1 | 10/2011 | Rezach | |
| 2011/0301650 A1 | 12/2011 | Johnson et al. | |
| 2012/0109208 A1 | 5/2012 | Justis et al. | |
| 2012/0221057 A1 | 8/2012 | Zhang et al. | |
| 2012/0271356 A1 | 10/2012 | Ramsay et al. | |
| 2013/0046345 A1 | 2/2013 | Jones et al. | |
| 2013/0090691 A1 | 4/2013 | Zhang et al. | |
| 2013/0096635 A1* | 4/2013 | Wall | A61B 90/92 606/305 |
| 2013/0238037 A1* | 9/2013 | Stad | A61B 17/708 606/86 A |
| 2013/0345759 A1 | 12/2013 | Meyer et al. | |
| 2014/0031871 A1 | 1/2014 | Fallin et al. | |
| 2014/0039557 A1* | 2/2014 | Stad | A61B 17/7077 606/279 |
| 2014/0135854 A1 | 5/2014 | Dec et al. | |
| 2014/0214084 A1 | 7/2014 | Jackson et al. | |
| 2014/0243605 A1 | 8/2014 | Gorek et al. | |
| 2014/0249591 A1* | 9/2014 | Peultier | A61B 17/7077 606/86 A |
| 2014/0277206 A1 | 9/2014 | Reitblat et al. | |
| 2014/0330315 A1 | 11/2014 | Butler et al. | |
| 2015/0051653 A1 | 2/2015 | Cryder et al. | |
| 2015/0066084 A1 | 3/2015 | Petit | |
| 2015/0066089 A1 | 3/2015 | Nelson et al. | |
| 2015/0094781 A1 | 4/2015 | Paroth et al. | |
| 2016/0113685 A1 | 4/2016 | Ishii et al. | |
| 2016/0345952 A1 | 12/2016 | Kucharzyk et al. | |

OTHER PUBLICATIONS

Extended European Search Report including the Written Opinion for Application No. EP 16835901.6 dated Jul. 1, 2019.

International Preliminary Report on Patentability and Written Opinion issued in International Application No. PCT/Udated Feb. 22, 2018.

Supplementary Partial European Search Report for EP16835901 dated Mar. 29, 2019.

* cited by examiner

EXTENDED TAB SYSTEMS FOR REDUCING SPINAL RODS

CROSS REFERENCE TO RELATED APPLICATIONS

This application is a continuation of U.S. patent application Ser. No. 15/752,142, filed Feb. 12, 2018, which is a national stage entry of International Application No. PCT/US2016/046523, filed Aug. 11, 2016, which claims the benefit of U.S. Provisional Patent Application No. 62/204,553, filed Aug. 13, 2015, the entire contents of which are incorporated by reference herein.

TECHNICAL FIELD

The present disclosure relates to spinal surgery. More specifically, the present disclosure relates to systems, devices, and methods for reducing spinal rods into pedicle screw housings.

BACKGROUND

The spinal column is a complex system of bones and connective tissues that provide support for the human body and protection for the spinal cord and nerves. The adult spine is comprised of an upper and lower portion. The upper portion contains 24 discrete bones, which are subdivided into three areas including 7 cervical vertebrae, 12 thoracic vertebrae and 5 lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury which restrict the range of motion of the spine or interfere with important elements of the nervous system. The problems include, but are not limited to scoliosis, kyphosis, excessive lordosis, spondylolisthesis, slipped or ruptured discs, degenerative disc disease, vertebral body fracture, and tumors. Persons suffering from any of the above conditions may experience extreme or debilitating pain and diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases. When the disc has degenerated to the point of requiring removal, there are a variety of interbody implants that are utilized to take the place of the disc. These include polyetheretherketone ("PEEK") interbody spacers, metal cages, and cadaver and human bone implants. In order to facilitate stabilizing the spine and keeping the interbody in position, other implants are commonly employed, including longitudinally linked rods secured to coupling elements, which in turn are secured to the bone by spinal bone fixation fasteners such as pedicle screws, hooks, and others. The opposing pair of longitudinally linked rods is commonly disposed along the long axis of the spine via a posterior approach. Pedicle screws are utilized to capture these rods and can be manufactured from any biocompatible material, including cobalt chrome, stainless steel, titanium, and PEEK. It is desired to perform these procedures in a minimally invasive manner to minimize pain and reduce recovery time for the patient.

Therefore, a need exists for a minimally invasive rod reducer that maintains proper screw and rod construct alignment.

SUMMARY

Accordingly, one aspect of the present disclosure is directed to a system for securing a spinal rod to a pedicle screw housing having wings. The wings define a rod-receiving passage. The wings, which may include a first wing and a second wing, define the rod-receiving passage between the first wing and the second wing. The rod-receiving passage is configured to receive the spinal rod therein. One or more tabs extend from each wing. Each tab may be coupled to one of the wings by one or more frangible members. One or more extensions may be secured to each tab.

In some embodiments, one or more tabs may be monolithically formed with the pedicle screw housing.

In certain embodiments, the pedicle screw housing and the tabs may be formed of a first material and the extensions may be formed of a second material. The first and second material may be different. The first material may include cobalt-chrome and the second material may include a titanium alloy.

In embodiments, the extensions may include a first extension and a second extension. The tabs may include a first tab and a second tab. The first extension may be coupled to the first tab and the second extension may be coupled to the second tab.

The frangible members may include a first frangible member and a second frangible member. The first frangible member may be coupled between the first extension and a first one of the wings. The second frangible member may be coupled between the second extension and a second one of the wings.

In some embodiments, one or more ring members may connect the extensions to the tabs.

In certain embodiments, the extensions and the ring members may include the same material. In embodiments, the extensions and the ring members may include a titanium alloy.

In embodiments, the system further includes a pedicle screw shank coupled to the pedicle screw housing.

According to another aspect, the present disclosure is directed to a rod reducer assembly. The rod reducer assembly includes a pedicle screw housing defining a rod-receiving passage therethrough, a tab removably coupled to the pedicle screw housing by a frangible member, and an extension secured to the tab. The extension and the tab may be separable from the pedicle screw housing upon application of a threshold force to the frangible member.

According to yet another aspect, the present disclosure is directed to a method of reducing a spinal rod. The method includes securing a pedicle screw housing to bone, guiding a spinal rod into the pedicle screw housing with a pair of extensions secured to tabs formed in the pedicle screw housing, and breaking the tabs off of the pedicle screw housing to separate the pair of extensions from the pedicle screw housing.

According to still another aspect of the present disclosure, a method for manipulating a pair of rod reducer assemblies mounted to bone is provided. The method comprises coupling a first leg of a modular compressor to a first rod reducer assembly, coupling a second leg of the modular compressor to a second rod reducer assembly, pivotally coupling the first and second legs of the modular compressor, and pivoting the first and second legs relative to one another to manipulate the first and second rod reducer assemblies relative to one another.

In accordance with one aspect of the present disclosure, a system for performing spinal surgery is provided. The system comprises one or more rod reducer assemblies and a modular compressor. The modular compressor including a first leg and a second leg that are pivotally coupled by a fulcrum assembly to selectively manipulate the one or more rod reducer assemblies.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein:

FIG. 13 is a cross-sectional view as taken along section line 13-13 delineated in

FIG. 12;

DETAILED DESCRIPTION

Figure 1:
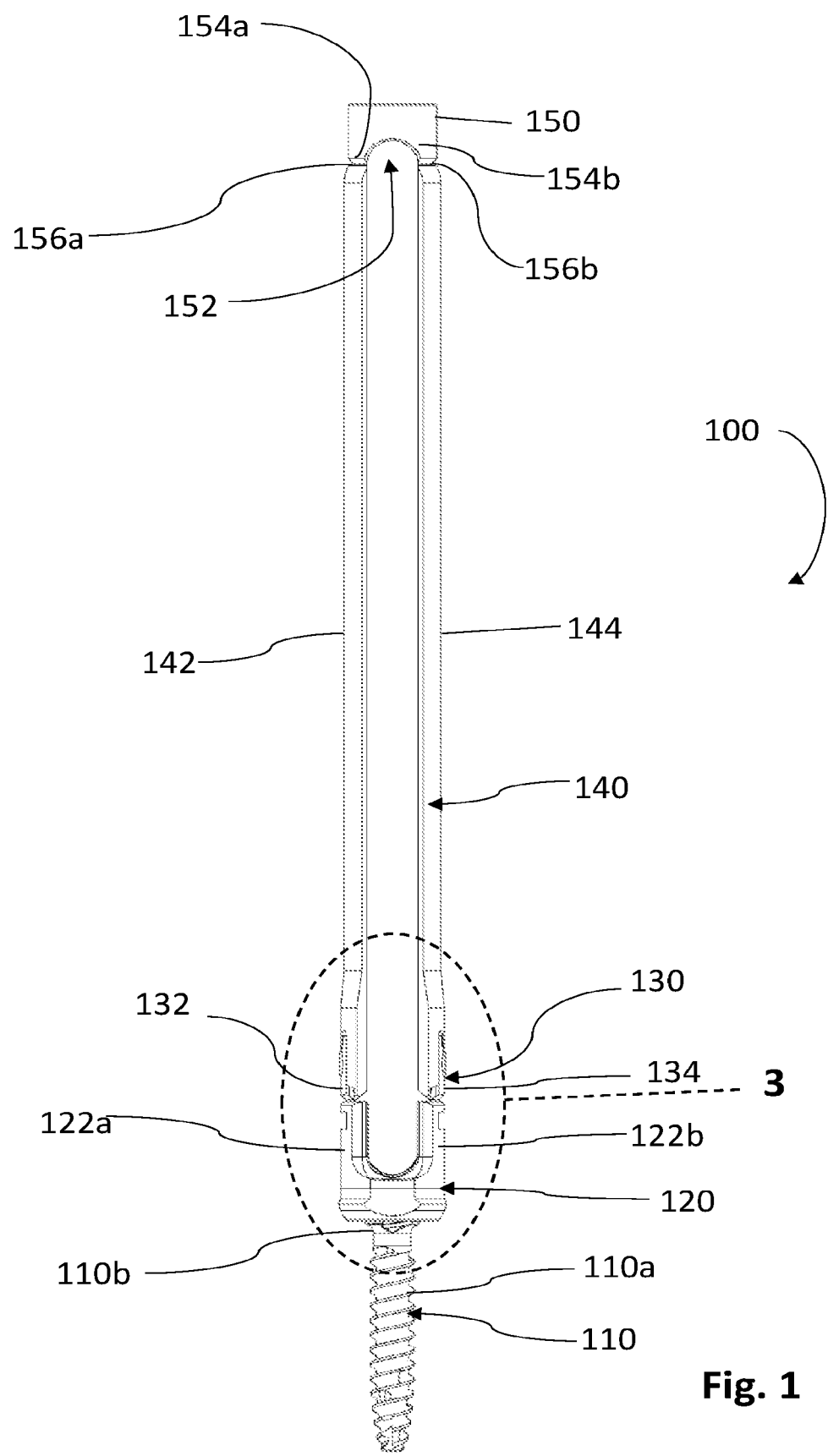
FIG. 1 is a front view of one embodiment of a rod reducer assembly.

Embodiments of the presently disclosed devices are described in detail with reference to the drawings, in which like reference numerals designate identical or corresponding elements in each of the several views. As used herein, the term "distal" or "leading" refers to that portion of the device that is farther from the user, while the term "proximal" or "trailing" refers to that portion of the device that is closer to the user.

Figure 2:
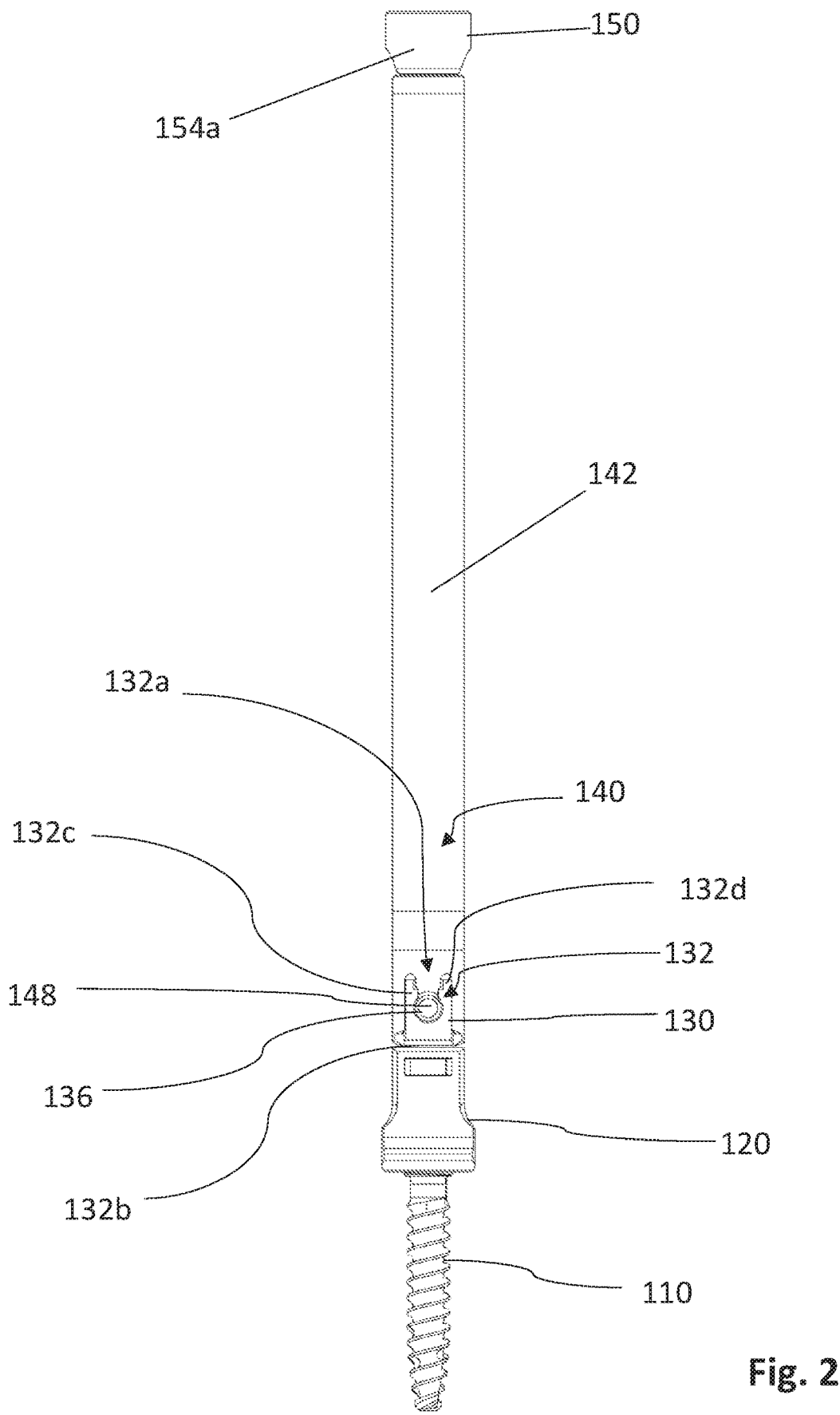
FIG. 2 is a side view of the rod reducer assembly of FIG. 1.
Figure 3:
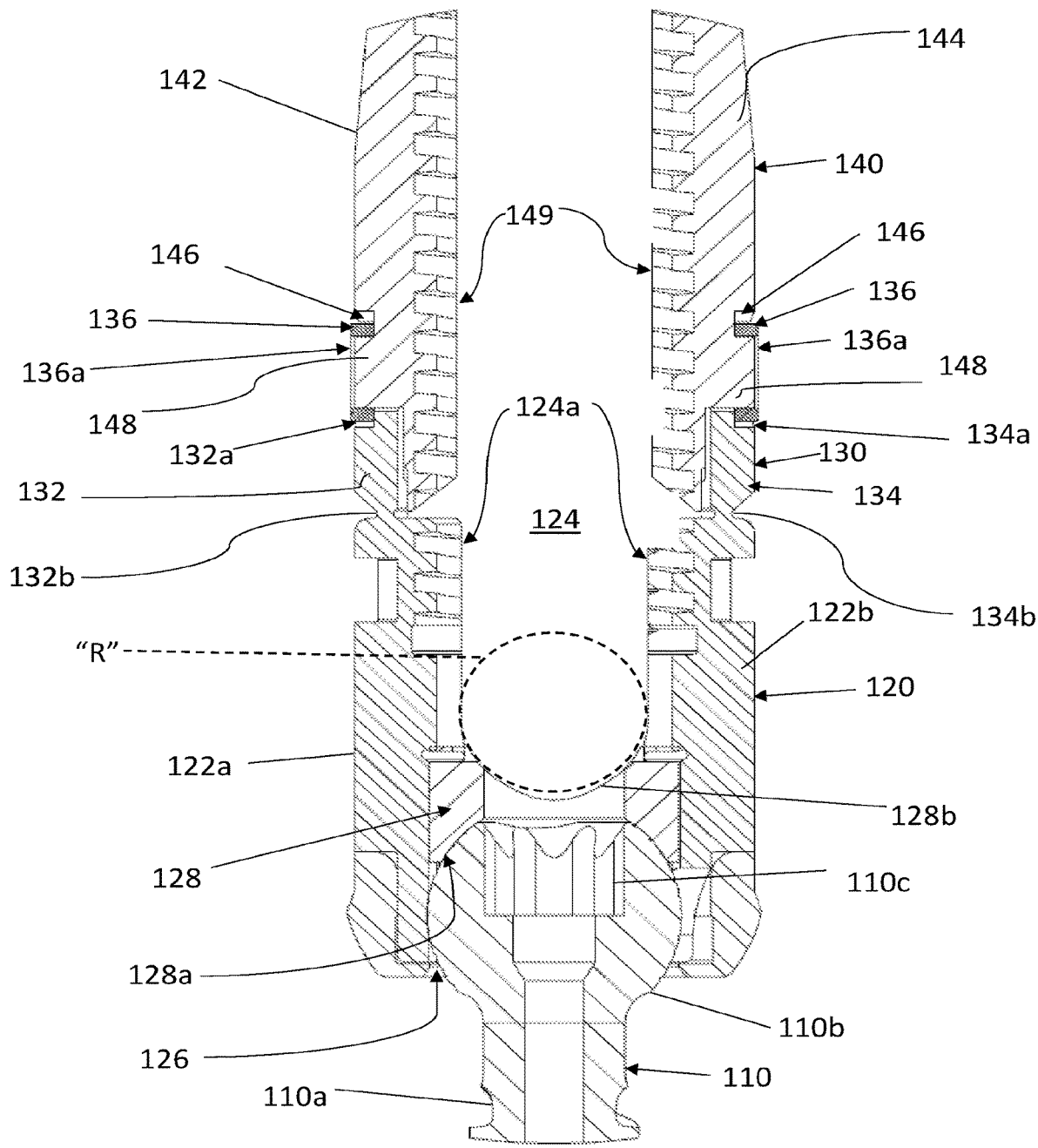
FIG. 3 is an enlarged, cross-sectional view of the indicated area of detail delineated in FIG. 1.

With reference to FIGS. 1-3, one embodiment of a rod reducer assembly 100 includes a pedicle screw 110, a pedicle screw housing 120 supported on a proximal or trailing end of the pedicle screw 110, a tab assembly 130 extending proximally from the pedicle screw housing 120, an extension assembly 140 coupled to the tab assembly 130 and extending proximally therefrom, and a head assembly 150 coupled to a proximal end of the extension assembly 140.

Figure 6:
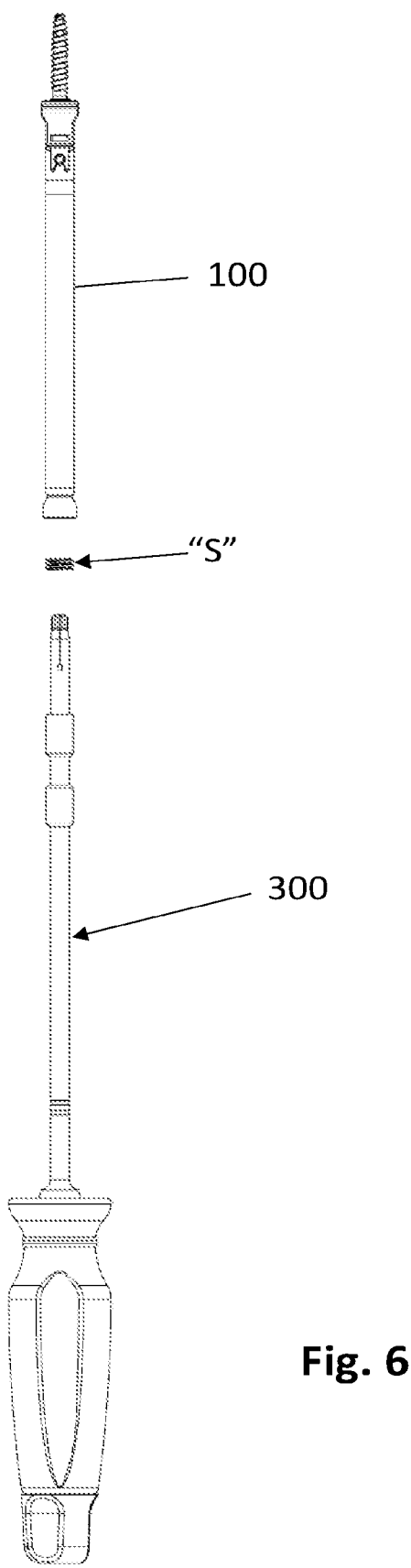
FIG. 6 is a side view, with parts separated, illustrating a split-tip driver, a set screw, and the rod reducer assembly of FIG. 1.
Figure 7:
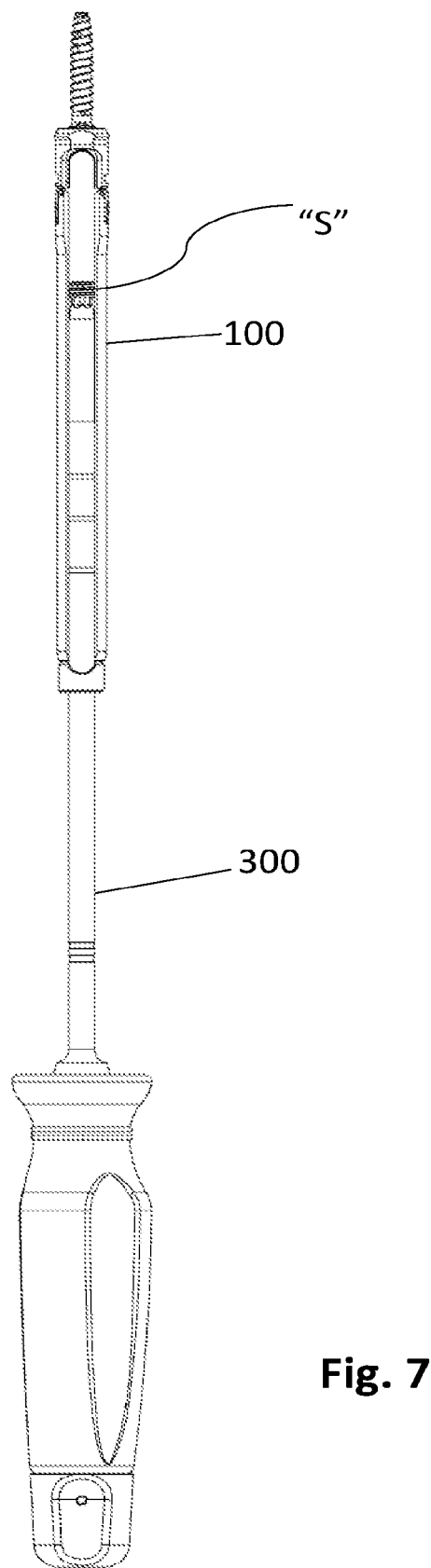
FIG. 7 is a front view illustrating the split-tip driver and the set screw received within the rod reducer assembly of FIG. 1.
Figure 8:
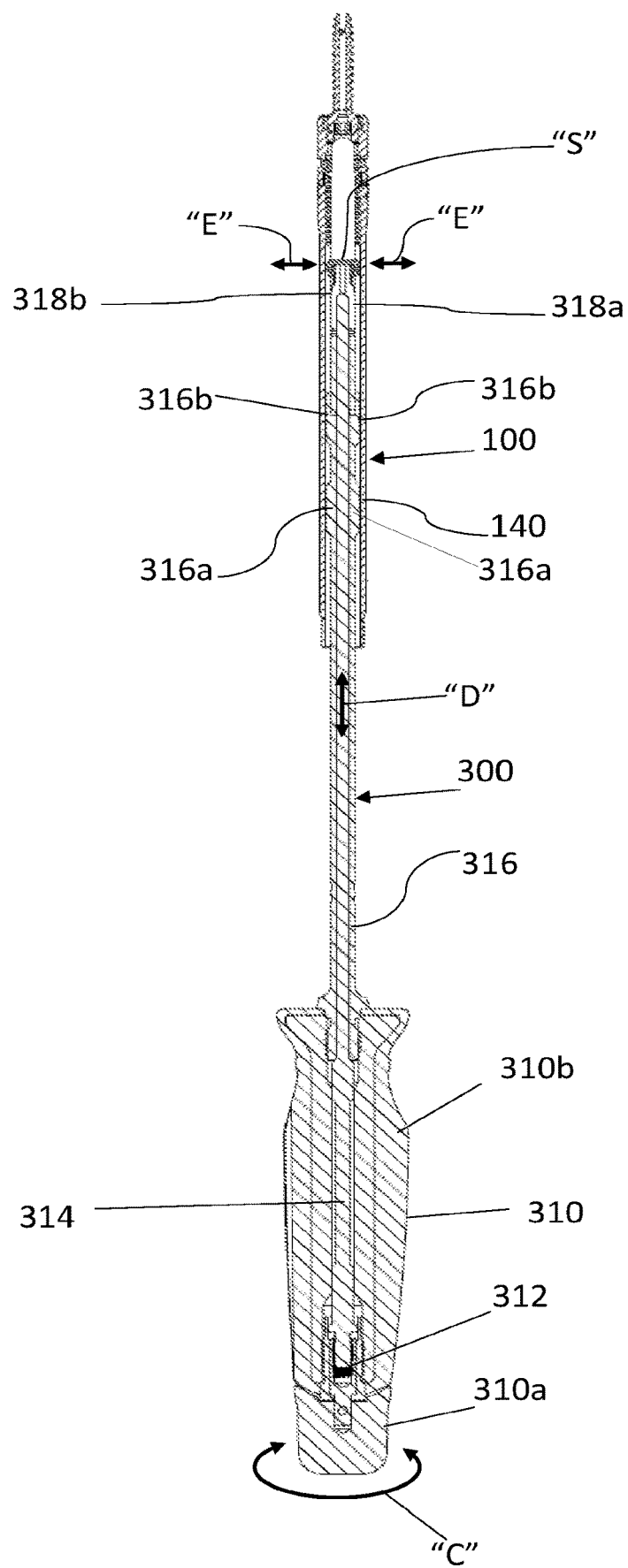
FIGS. 8 and 9 are front and side cross-sectional views, respectively, illustrating the split-tip driver and the set screw received within the rod reducer assembly of FIG. 1.
Figure 9:
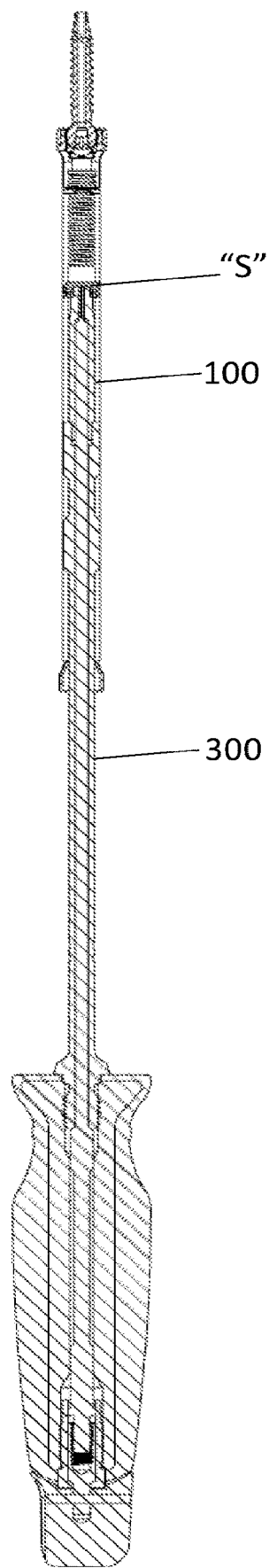

The pedicle screw 110 has a threaded shank 110a and a head 110b supported on the threaded shank 110a. The head 110b defines a drive recess 110c, which may be any suitable shape such as hexolobular or the like. The drive recess 110c is configured to selectively receive a drive tool (not shown) such as a screw driver to rotate the threaded shank 110a of the pedicle screw 110 into bone. The pedicle screw housing 120 is U-shaped and includes a pair of wings 122a, 122b that defines a U-shaped rod-receiving passage 124 at a proximal end of the pedicle screw housing 120. A threaded internal surface 124a is defined by the pair of wings 122a, 122b and is configured to threadably receive a set screw "S" (see FIG. 6) therein to engage and secure the spinal rod "R" within the pedicle screw housing 120. The pedicle screw housing 120 further defines a concave recess 126 in a distal end thereof that receives the head 110b of the pedicle screw 110. An anvil 128 is also received within pedicle screw housing 120 and includes a distal recess 128a that receives the proximal end of the head 110b of the pedicle screw 110 while the head 110b is disposed within the concave recess 126 of the pedicle screw housing 110b. The anvil 128 further defines a saddle 128b on a proximal end thereof that supports a spinal rod "R" thereon. For a more detailed description of similar pedicle screw assemblies, reference can be made, for example, to U.S. Pat. No. 8,882,817, the entire contents of which are incorporated by reference herein.

The tab assembly 130 includes a pair of tabs 132, 134, each tab of which may be disposed in mirrored relation with the other tab of the pair of tabs 132, 134. The tab 132 defines a recess 132a that separates the tab 132 into a pair of arms 132c, 132d at a proximal end of the tab 132. The tab 132 further includes a frangible member 132b secured to the wing 122a at a distal end of the tab 132. The tab 134 includes a recess 134a that separates tab 134 into a pair of arms (not shown but identical to the pair of arms 132c, 132d) at a proximal end of the tab 132. The tab 134 further includes a frangible member 134b secured to a wing 122b at a distal end of the tab 134. The frangible members 132b, 134b may be integrally and/or monolithically formed with respective wings 122a, 122b. The frangible members 132b, 134b may be configured to break upon application of a threshold force thereto (e.g., twisting, bending, tensile, and/or shear forces) to enable the tabs 132, 134 to separate from the wings 122a, 122b. As used herein, the term "break" (or its equivalent) refers to rupturing, dividing, tearing, fracturing, splitting, and/or the like. Each of the recesses 132a, 134a receives a ring member or ring 136 therein to couple the extension assembly 140 thereto.

Figure 13:
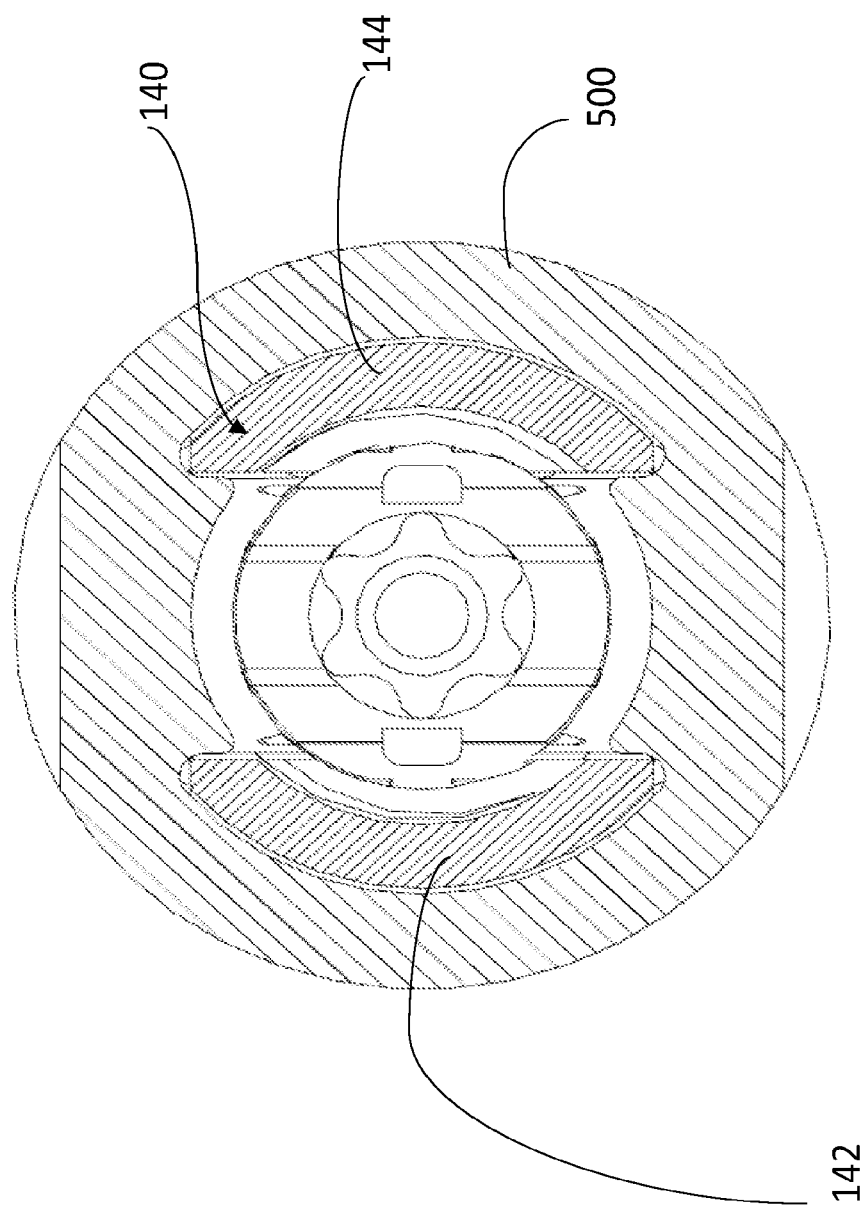
Figure 14:
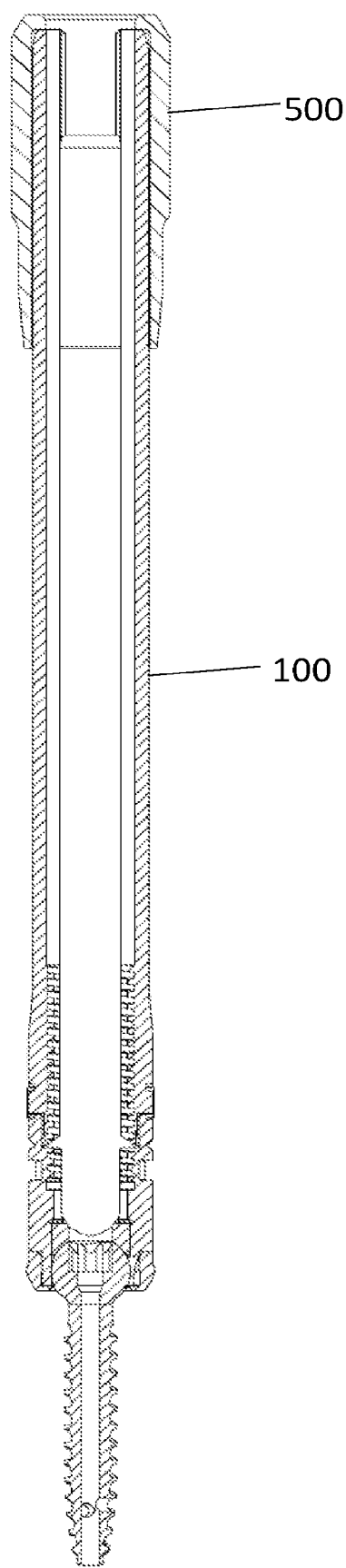
FIG. 14 is a front, cross-sectional view illustrating the reducer cap positioned on the rod reducer assembly as shown in FIG. 12 with the head portion of the rod reducer assembly removed.

The extension assembly 140 includes a pair of extensions 142, 144 coupled to the tabs 132, 134 by rings 136. Each of the pair of extensions 142, 144 defines a recess 146 in distal end portion thereof and is curved inwardly to define an elongate channel there along (see FIG. 13). Each recess 146 receives one of the tabs 132, 134 and one of the rings 136 therein. A protuberance 148 extends from the recess 146 and is receivable through an opening 136a defined by the ring 136. The extension assembly 140 further includes an internal threaded surface 149 in vertical registration with the threaded internal surface 124a of the pedicle screw housing 120. The internal threaded surfaces 149 threadably receives the set screw "S" (FIG. 6) and facilitates threaded reception of the set screw "S" into the pedicle screw housing 120 via the threaded internal surface 124a of the pedicle screw housing 120.

Head assembly 150 defines an inverted U-shape recess 152 that separates a pair of arms 154a, 154b of the head assembly 150. Distal ends of the pair of arms 154a, 154b are coupled to proximal ends of the extensions 142, 144 of the extension assembly 140 by the frangible members 156a, 156b. Similar to the frangible members 132b, 134b of the tab assembly 130, the frangible members 156a, 156b are configured to break upon application of a threshold force thereto to separate the head assembly 150 from the extension assembly 140 as desired.

Figure 4:
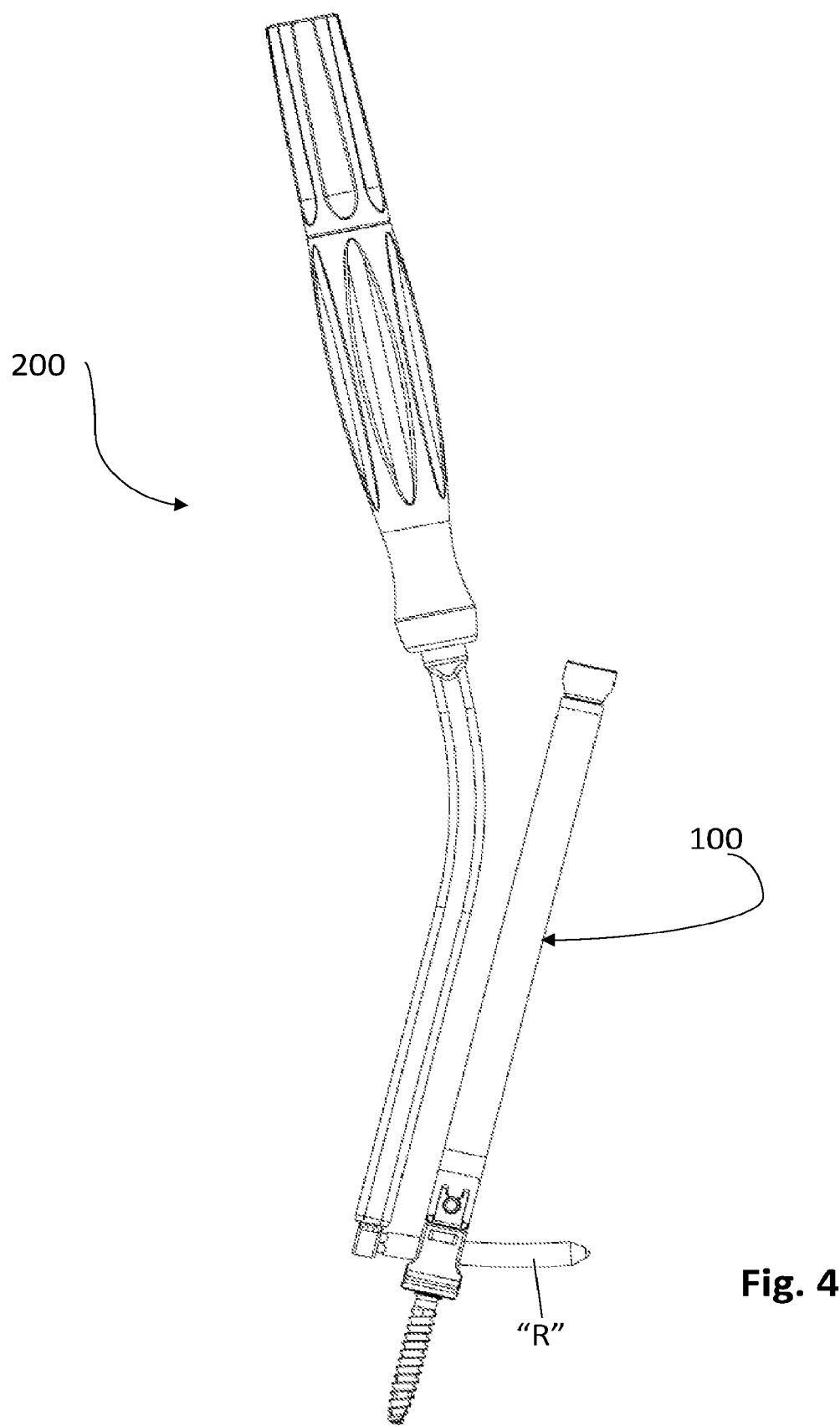
FIGS. 4 and 5 are side views illustrating the rod reducer assembly of FIG. 1, a spinal rod, and a rod inserter.
Figure 5:
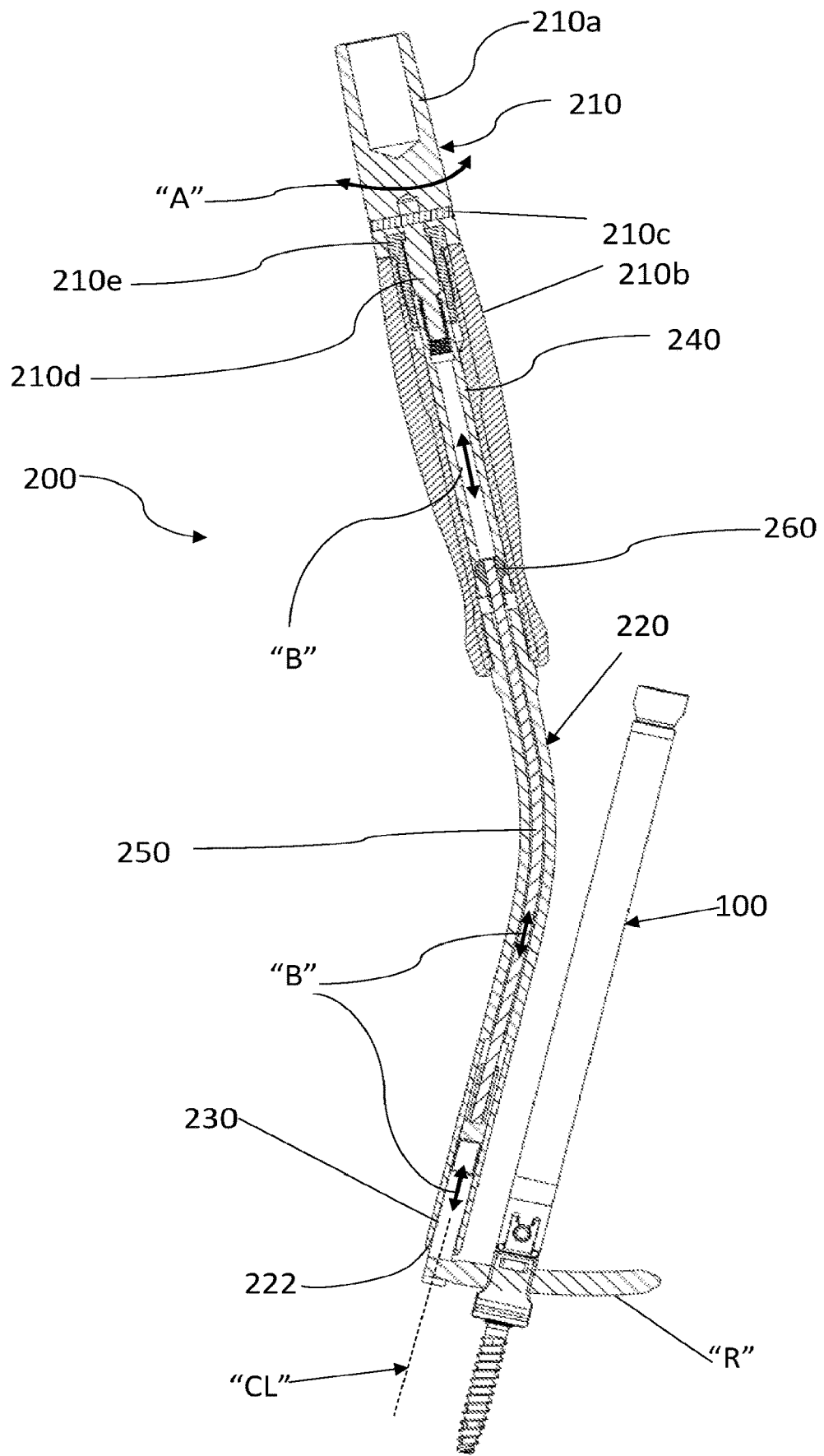

Turning now to FIGS. 4 and 5, a rod inserter 200 can be used to insert a spinal rod "R" into the rod reducer assembly 100. The rod inserter 200 includes a handle assembly 210 having a proximal handle 210a and a distal handle 210b. The proximal and distal handles 210a, 210b are coupled together by a rotation ring 210c and coupling members 210d, 210e. An elongate tubular shaft member 220 extends distally from the handle assembly 210 and includes a distal end that has an inner ramp 222. The handle assembly 210 and the elongate tubular shaft 210, 220 support an inner shaft 240 and a connector member 250 (e.g., a cable and/or a shaft). The inner shaft 240 and the connector member 250 are coupled together via a ball fitting 260 coupled to a proximal end of the connector member 250, for example, via crimping. A distal end of connector member 250 is coupled to a working end 230 configured to selectively grasp the spinal rod "R."

In use, the rotation ring 210c enables the proximal handle 210a to rotate relative to the distal handle 210b, as indicated by arrows "A." Rotation of the proximal handle 210a causes the inner shaft 240, the connector member 250, and the working end 230 to translate along a centerline "CL" of the rod inserter 200 as indicated by arrows "B." Proximal movement of the working end 230 along the centerline "CL" into the elongated tubular shaft member 220 tightens working end 230 around the spinal rod "R" as the working end 230 engages the inner ramp 222 and loosens the working end 230 around the spinal rod "R" in response to distal movement of the working end 230. The working end 230 may be spilt. For a more detailed description of similar rod inserters, reference can be made, for example, to U.S. Patent Application Publication 2013/0345759, the entire contents of which are hereby incorporated by reference herein.

Turning now to FIGS. 6-9, a split-tip driver 300 can be used to insert the set screw "S" into the rod reducer assembly 100, for example, after the spinal rod "R" (FIG. 5) is positioned within the rod reducer assembly 100 to secure the spinal rod "R" to the rod reducer assembly 100. The split-tip driver 300 includes a driver handle assembly 310 having a proximal handle member 310a rotatably mounted to a distal handle member 310b by a threaded coupling feature 312. A proximal end of an inner shaft 314 is threadably coupled to the threaded coupling feature 312. An outer tubular shaft 316 extends from a distal end of the handle assembly 310 and slidably receives the inner shaft 314 therein. The outer tubular shaft 316 extends to tips 318a, 318b pivotably coupled at a distal end of the outer tubular shaft 316. The tips 318a, 318b are split and biased to move radially inwards toward one another. The outer tubular shaft 316 and further includes guide nubs 316a, 316b that support the outer tubular shaft 316 within the extension assembly 140 of the rod reducer assembly 100.

In use, the proximal handle member 310a rotates relative to the distal handle member 310b, as indicated by arrows "C," to slide the inner shaft 314 longitudinally along a centerline (not shown) of the split-tip driver 300 and through the outer shaft 316, as indicated by arrows "D." The tips 318a, 318b, which are receivable within the set screw "S" to hold the set screw "S," are configured to move between radially inward and radially outward directions, as indicated by arrows "E," in response to the rotation of the proximal handle member 310a relative to the distal handle member 310b. In particular, distal movement of the inner shaft 314 relative to the outer shaft 316 moves the tips 318a, 318b radially outwardly, separating the tips 318a, 318b from one another and enabling the tips 318a, 318b to hold the inner surface of the set screw "S" (e.g., via friction fit). In contrast, proximal movement of the inner shaft 314 relative to the outer shaft 316 enables the tips 318a, 318b to move radially inwardly (e.g., the tips 318a, 318b are biased to move toward one another) so that the tips 318a, 318b can separate from the inner surface of the set screw "S."

Figure 10:
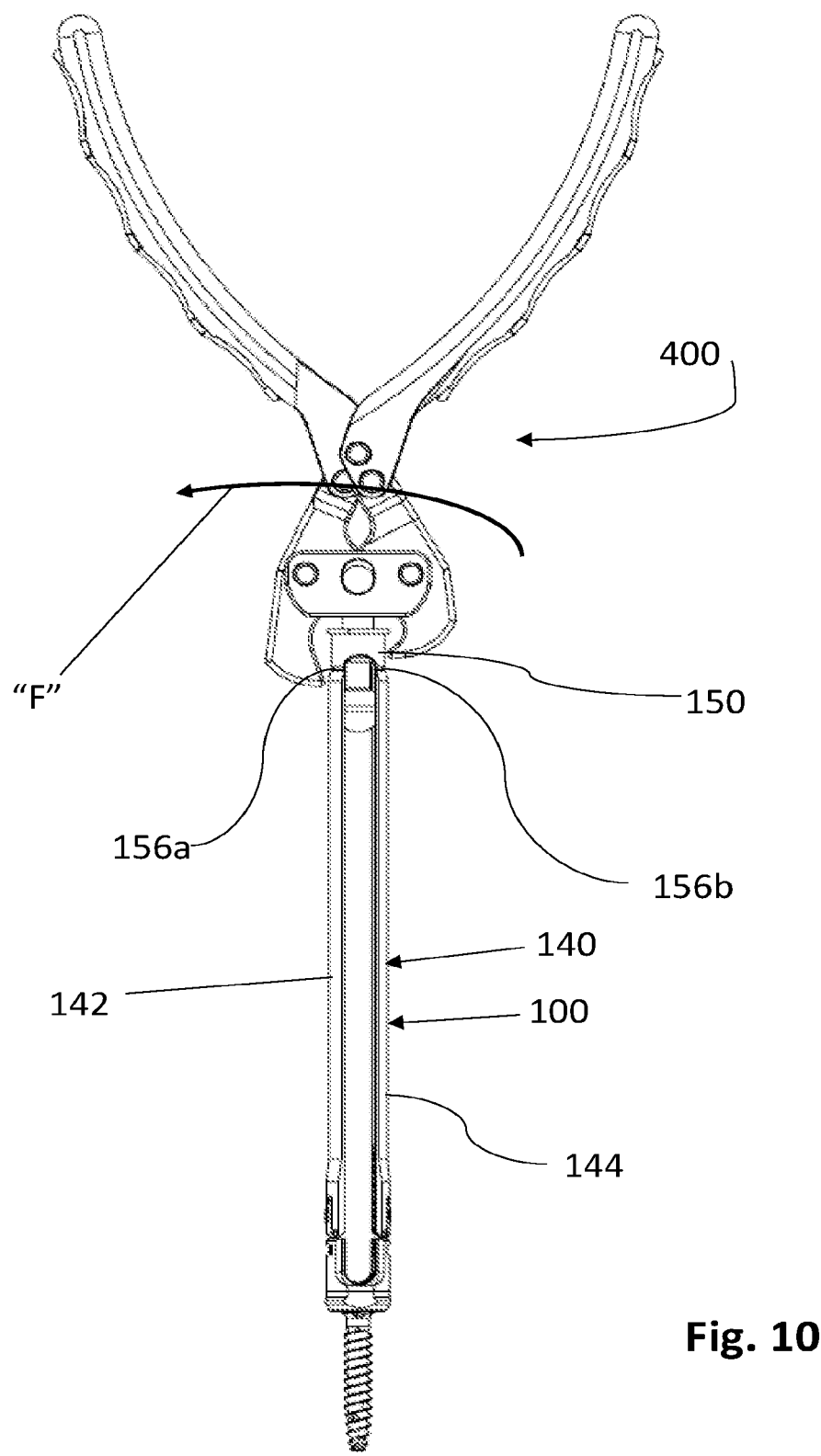
FIG. 10 is a front view illustrating pliers and the rod reducer assembly of FIG. 1, the pliers shown positioned on the rod reducer assembly.
Figure 11:
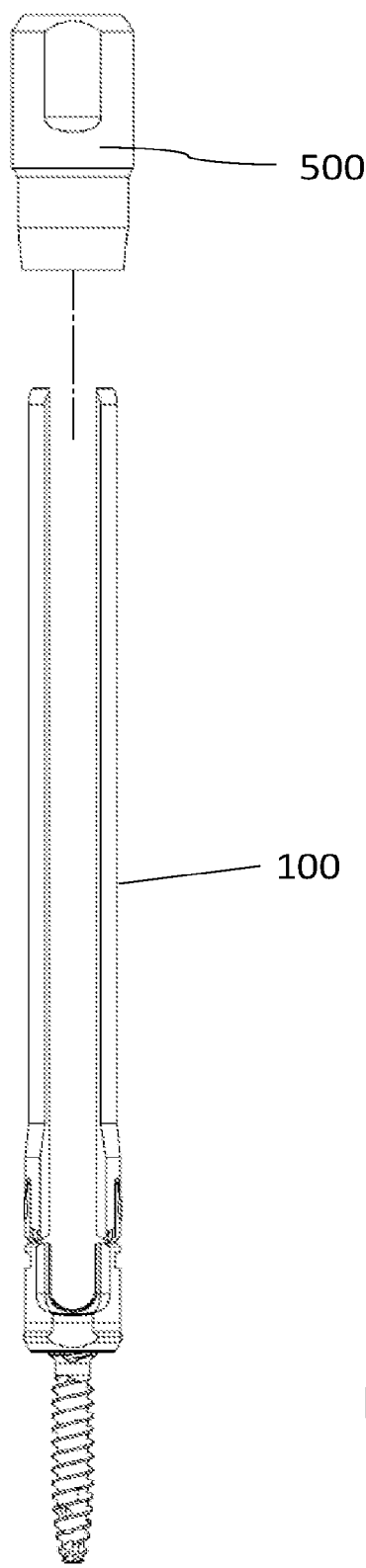
FIG. 11 is a front view illustrating a reducer cap and the rod reducer assembly of FIG. 1, the reducer cap shown separate from the rod reducer assembly, the rod reducer assembly having a head portion thereof removed.
Figure 12:
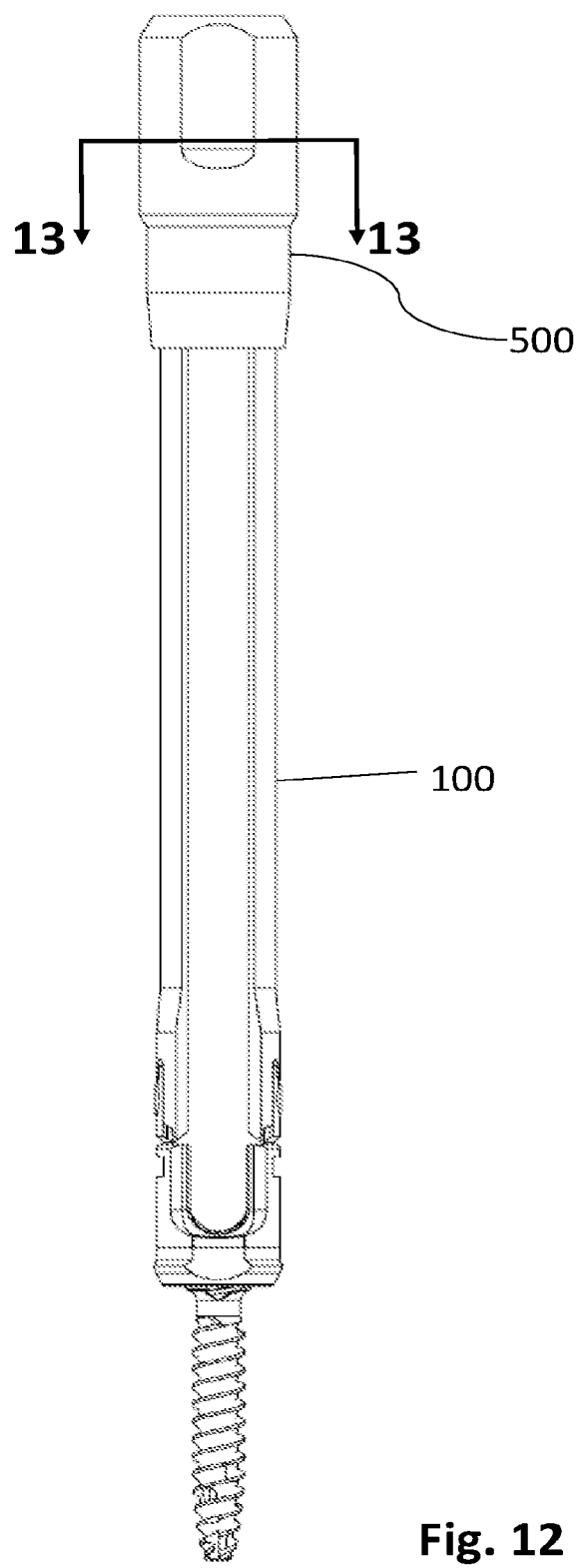
FIG. 12 is a front view illustrating the reducer cap, the reducer cap shown positioned on the rod reducer assembly with the head portion of the rod reducer assembly removed.

With reference to FIG. 10, a pair of pliers 400 or the like can be used to separate the head assembly 150 of the rod reducer assembly 100 from the extension assembly 140 of the rod reducer assembly 100, as desired. For example, the pliers 400 can be used to break the frangible members 156a, 156b of the head assembly 150 from the extensions 142, 144 of the extension assembly 140 by grasping the head assembly 150 and rotating the head assembly 150 away from the extension assembly 140 as indicated by arrow "F."

As seen in FIGS. 11-14, once the head assembly 150 of the rod reducer assembly 100 is separated from the extension assembly 140 of the rod reducer assembly 100, a clinician can mount a tubular cap member 500 onto the proximal end of the extension assembly 140 as desired to support the extension assembly 140 and maintain a parallel arrangement of the extensions 142, 144 of the extension assembly 140 relative to one another to enable rod reduction while limiting splay.

Figure 15:
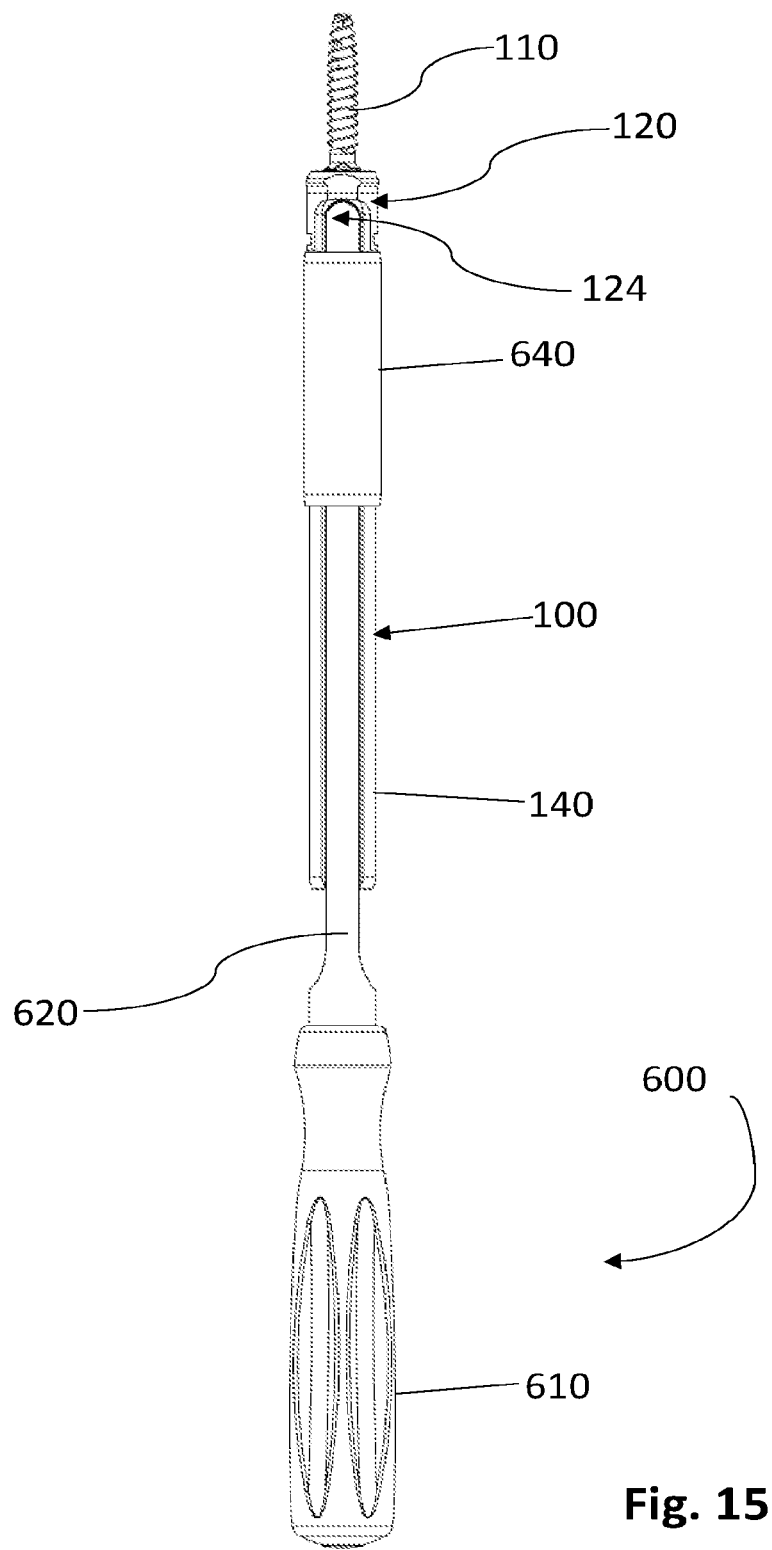
FIG. 15 is a front view illustrating one embodiment of a tab breaker, the tab breaker shown positioned on the rod reducer assembly of FIG. 1 with the head portion of the rod reducer assembly removed.
Figure 16:
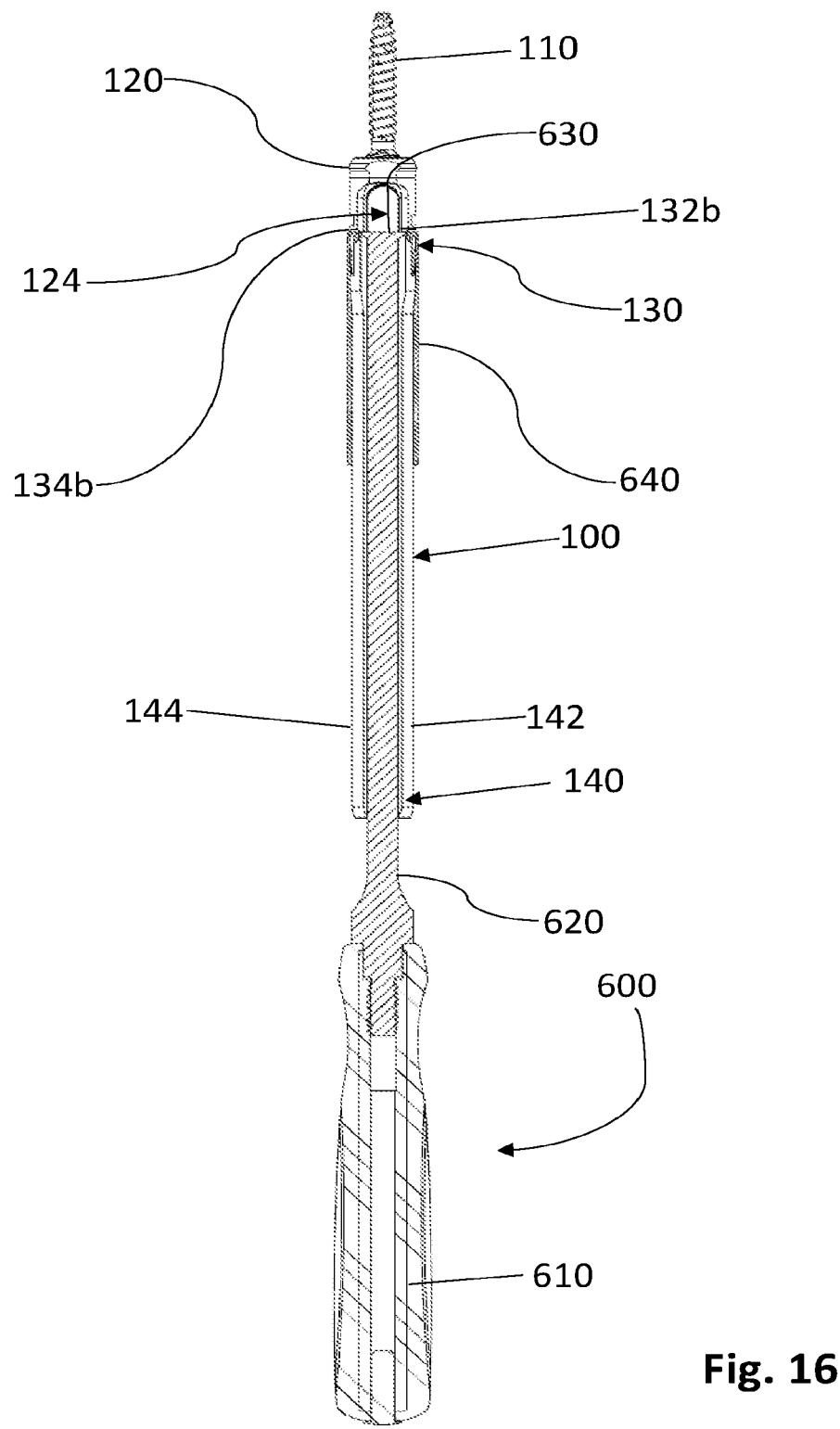
FIG. 16 is a front, cross-sectional view illustrating the tab breaker of FIG. 15 positioned on the rod reducer assembly of FIG. 1 with the head portion of the rod reducer assembly removed.

Turning now to FIGS. 15-16, one embodiment of a tab breaker system, referred to as tab breaker 600, can be utilized to separate the tab and extension assemblies 130, 140 of the rod reducer assembly 100 from the pedicle screw housing 120 of the rod reducer assembly 100 as desired. Tab breaker system 600 includes a handle 610, an elongate shaft 620 that extends distally from the handle 610, and a blunt tip 630 supported on a distal end of the elongate shaft 620. The tab breaker system 600 further includes a tubular sleeve 640.

In use, the elongate shaft 620 of the tab breaker system 600 is advanced between the pair of extensions 142, 144 and the tubular sleeve 640 is advanced along an outer surface of the pair of extensions 142, 144. The tubular sleeve 640 can be positioned adjacent to the pedicle screw housing 120 and in contact with the tab assembly 130. The tab breaker system 600, or components thereof, can then be manipulated (e.g., pivoted, rotated, etc.) as necessary to break the frangible members 132b, 134b of the tab assembly 130, for example, with the pedicle screw 110 secured to bone and a spinal rod (not shown) supported within the U-shaped rod-receiving passage 124 of the pedicle screw housing 120. Once the frangible members 132b, 134b of the tab assembly 130 are broken, the tab assembly 130, the extension assembly 140, and the tab breaker system 600 can be separated from the pedicle screw housing 120.

Figure 17:
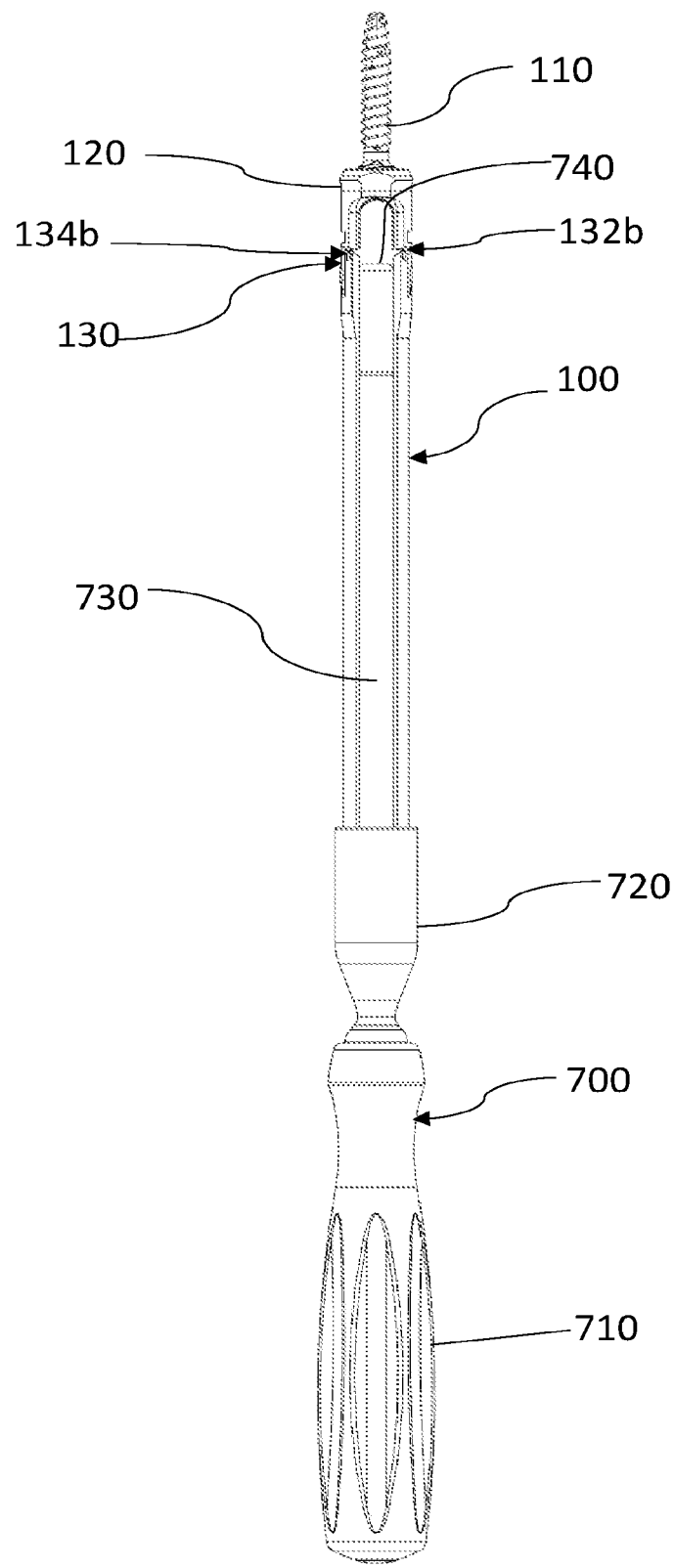
FIG. 17 is a front view illustrating another embodiment of a tab breaker, the tab breaker shown positioned on the rod reducer assembly of FIG. 1 with the head portion of the rod reducer assembly removed.
Figure 18:
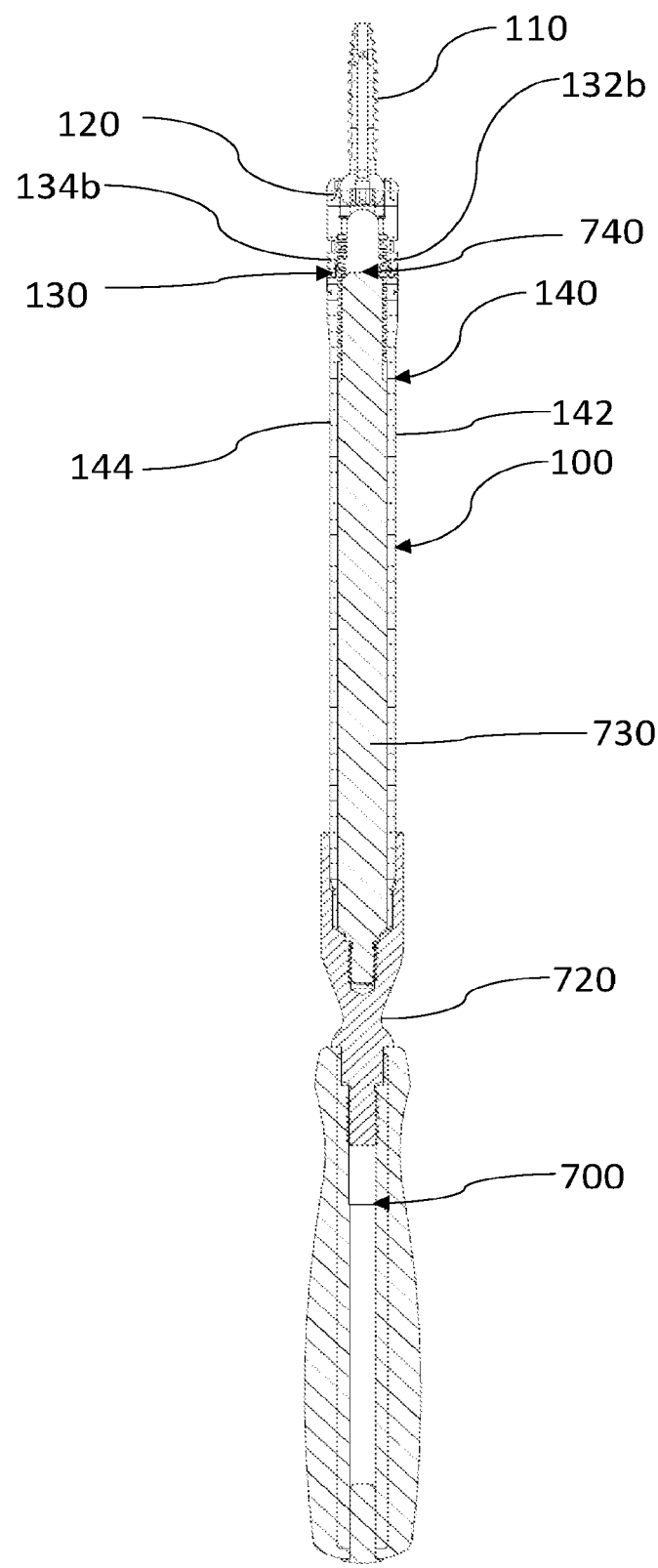
FIG. 18 is a front, cross-sectional view illustrating the tab breaker of FIG. 17 positioned on the rod reducer assembly of FIG. 1 with the head portion of the rod reducer assembly removed.
Figure 19:
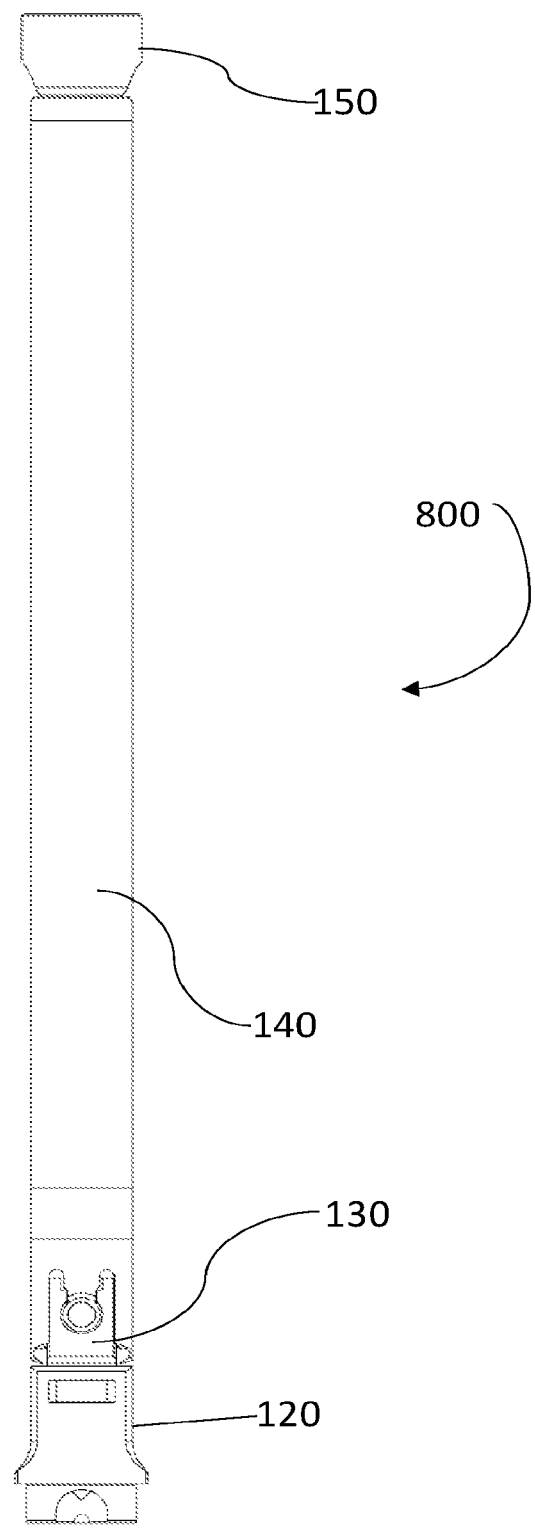
FIG. 19 is a side view another embodiment of a rod reducer assembly.
Figure 20:
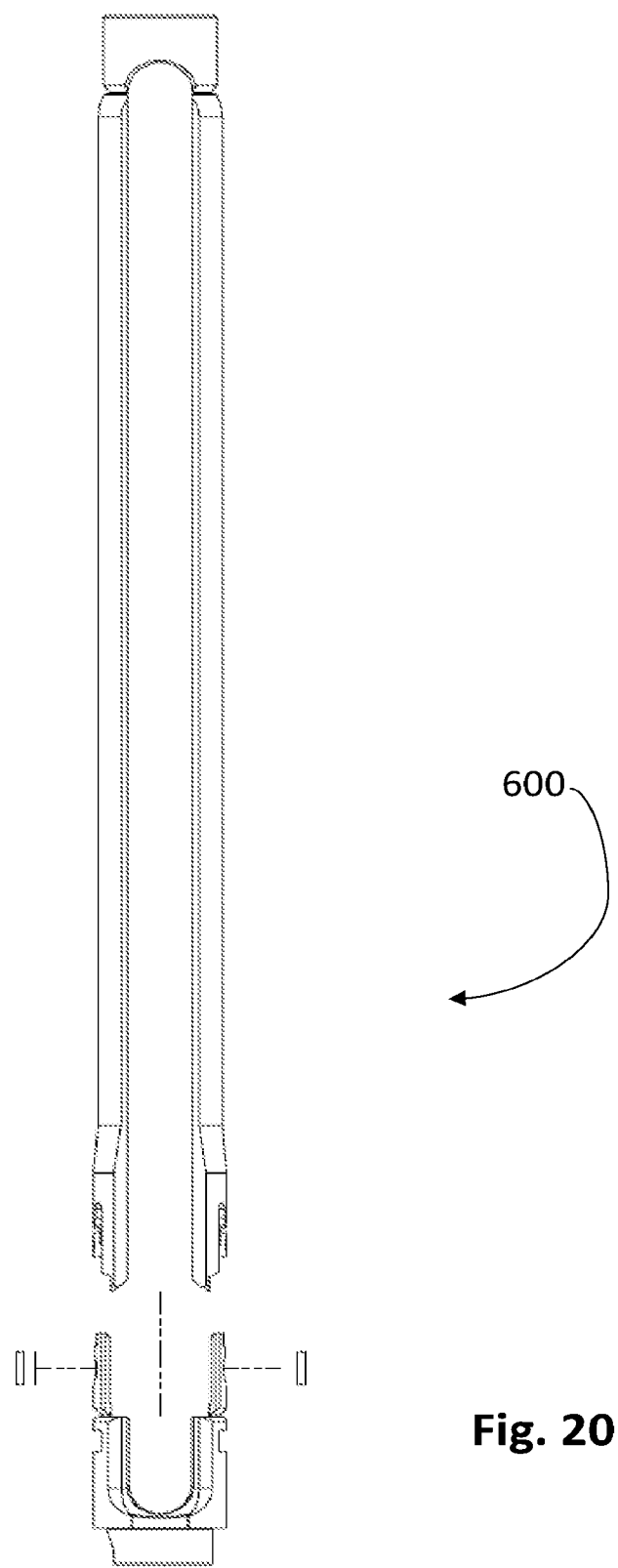
FIG. 20 is a front view, with parts separated, of the rod reducer assembly of FIG. 19.
Figure 21:
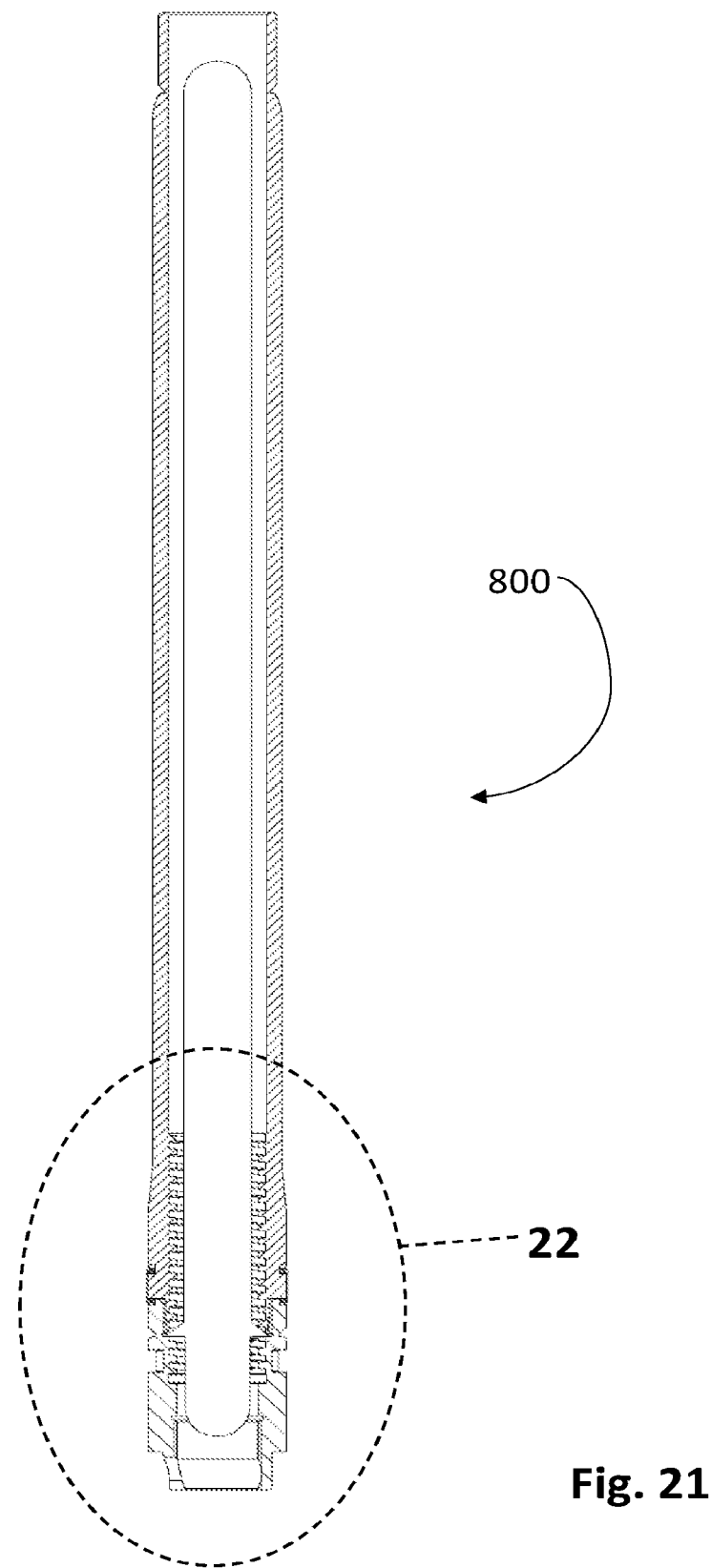
FIG. 21 is a front, cross-sectional view of the rod reducer assembly of FIG. 19.
Figure 22:
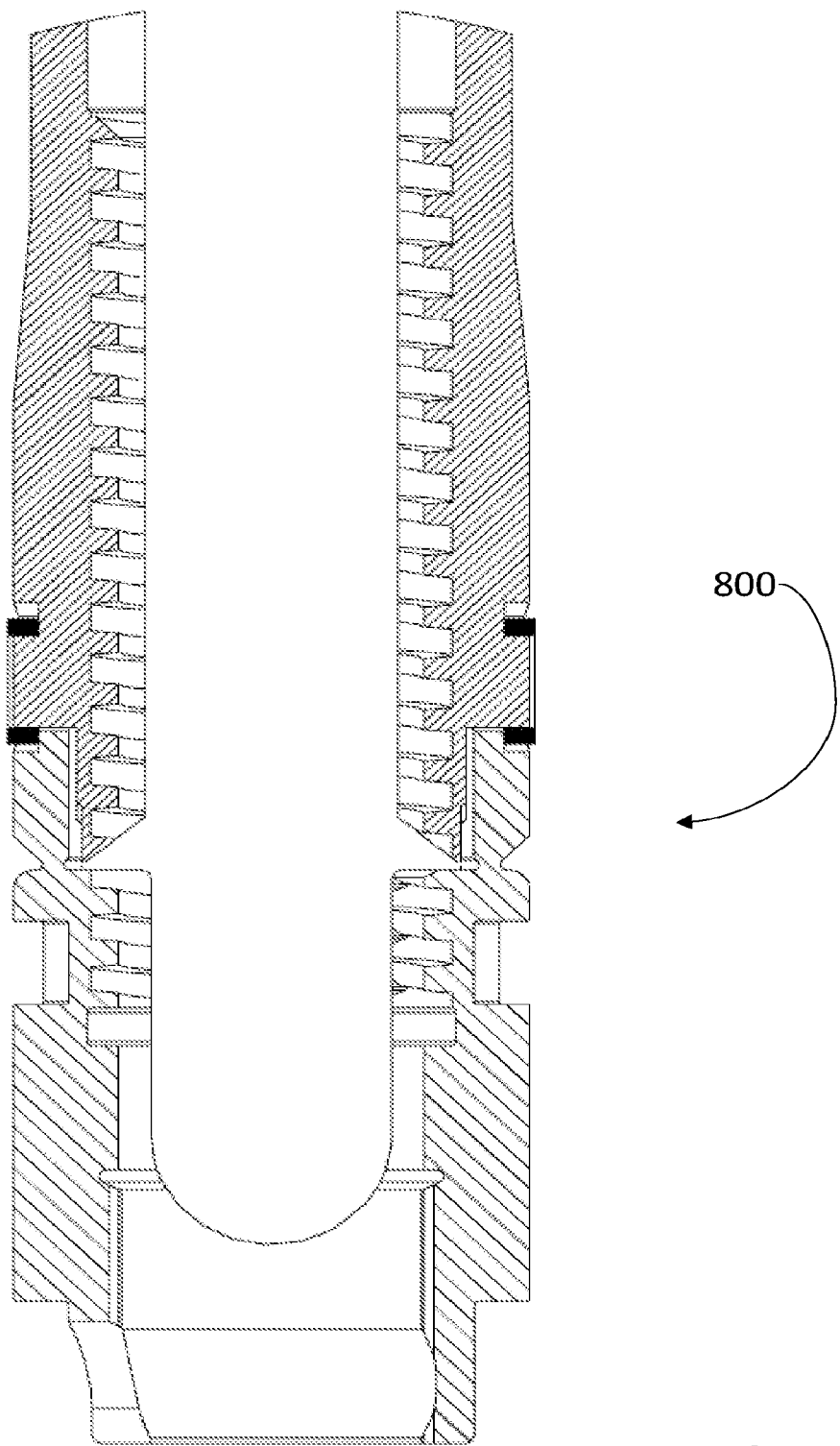
FIG. 22 is an enlarged view of the indicated area of detail delineated in FIG. 21.
Figure 23:
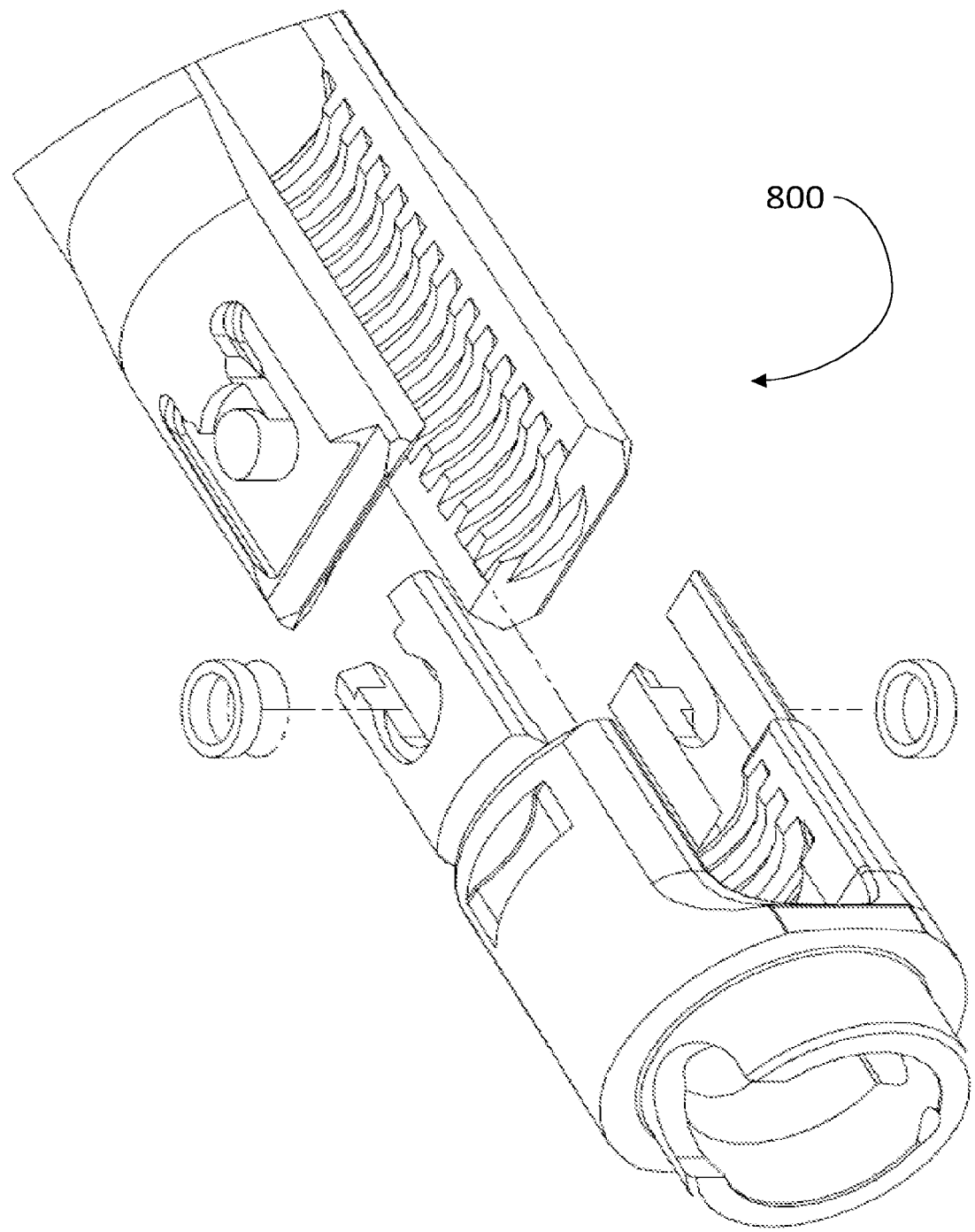
FIG. 23 is an enlarged, perspective view, with parts separated of a portion of the rod reducer assembly of FIG. 19.

As seen in FIGS. 17 and 18, another embodiment of a tab breaker system, referred to as tab breaker system 700 is provided. The tab breaker system 700 includes a handle 710, a coupling portion 720 having a proximal end secured to a distal end of the handle 710, and an elongate shaft 730 extending distally from a distal end of the coupling portion 720 to a blunt tip 740.

In use, the elongate shaft 730 of the tab breaker system 700 is advanced between the pair of extensions 142, 144 of the extension assembly 140 and the coupling portion 730 is advanced over the proximal end of the extensions 142, 144. With the coupling portion 730 and the elongate shaft 730 of the tab breaker system 700 secured to the extension assembly 140, the tab breaker system 700 can be manipulated as necessary to break the frangible members 132b, 134b of the tab assembly 130 similar to that described above with respect to the tab breaker system 600.

FIGS. 19-23 illustrate another embodiment of a rod reducer assembly, referred to as rod reducer assembly 800. The rod reducer assembly 800 is substantially similar to the rod reducer assembly 100 without the pedicle screw thereof. In general, the rod reducer assembly 800 includes a pedicle screw housing 120, a tab assembly 130 extending proximally from the pedicle screw housing 120, an extension assembly 140 coupled to the tab assembly 130 and extending proximally therefrom, and a head assembly 150 coupled to a proximal end of the extension assembly 140.

Figure 24:
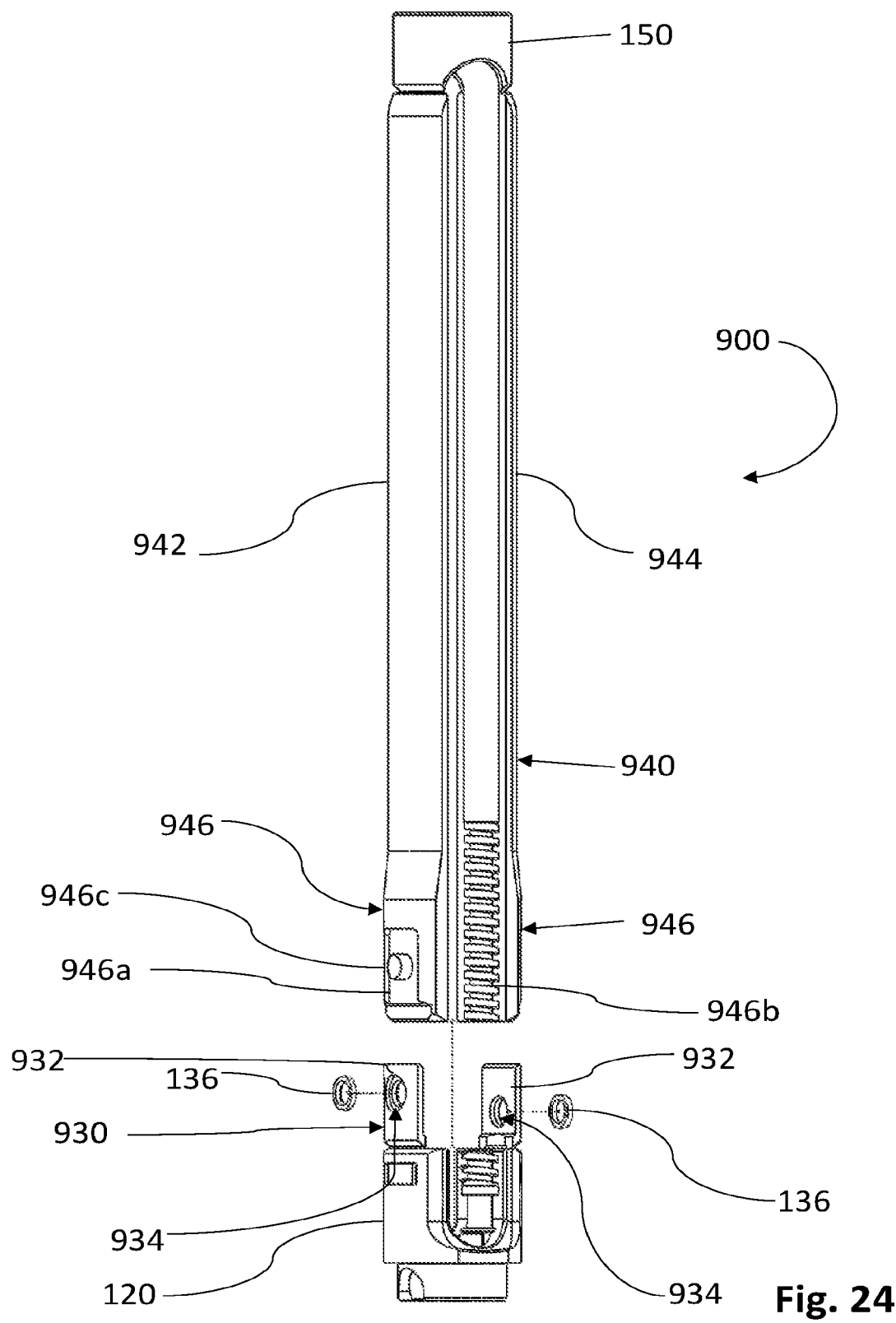
FIG. 24 is a perspective view, with parts separated, of another embodiment of a rod reducer assembly.
Figure 25:
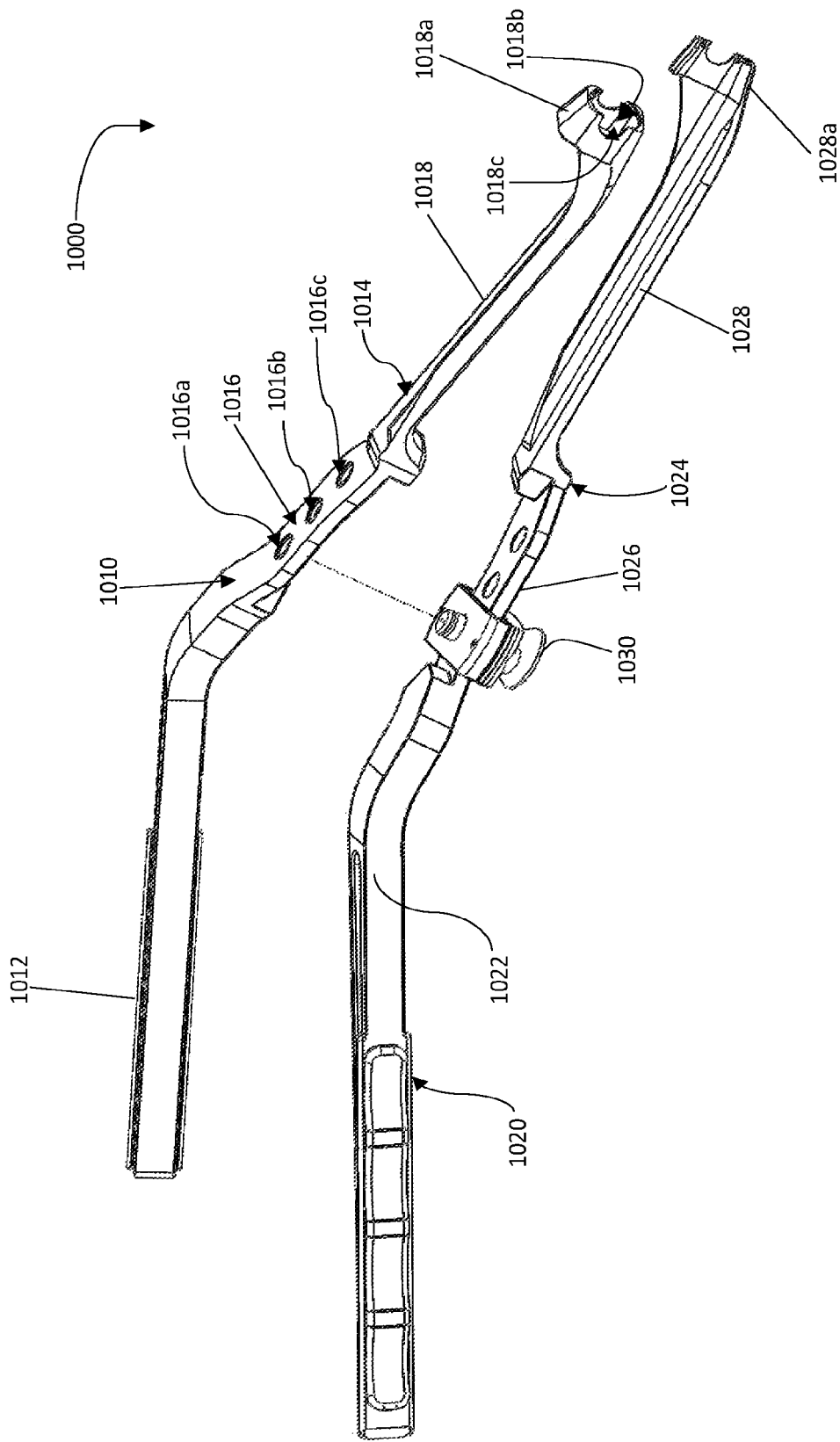
FIG. 25 is a perspective view, with parts separated, of a modular compressor.
Figure 26:
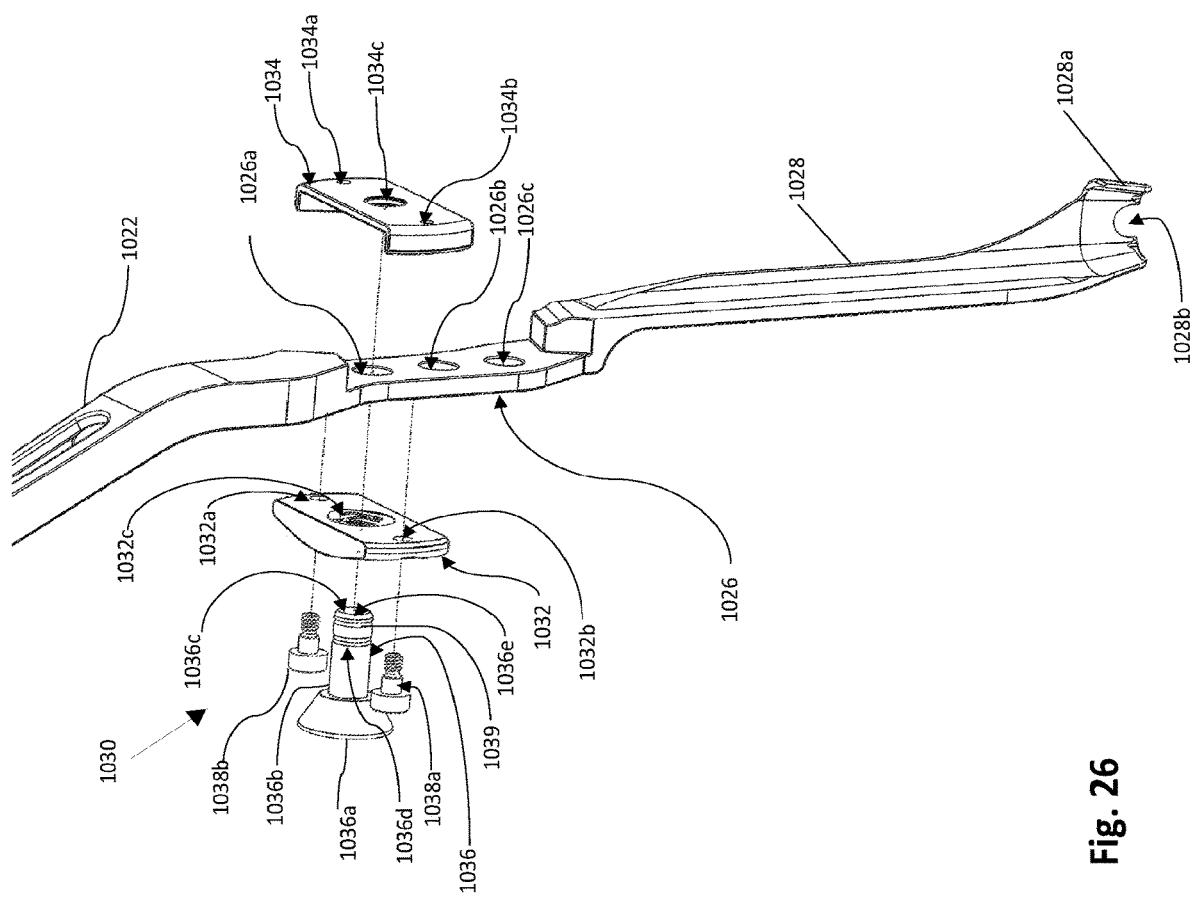
FIG. 26 is a perspective view, with parts separated, of a fulcrum assembly and one leg of the modular compressor of FIG. 25.

FIG. 24 is yet another embodiment of a rod reducer assembly, referred to as rod reducer assembly 900. The rod reducer assembly 900 is substantially similar to the rod reducer assembly 800. In particular, rod reducer assembly 900 illustrates that rod reducer assemblies of the present disclosure, or components thereof (e.g., extension and/or tab assemblies), can have any suitable configuration. In general, the rod reducer assembly 900 includes a pedicle screw housing 120, a tab assembly 930 extending proximally from the pedicle screw housing 120, an extension assembly 940 coupled to the tab assembly 930 and extending proximally therefrom, and a head assembly 150 coupled to a proximal end of the extension assembly 940. The tab assembly 930 includes tabs 932, which may have any suitable shape such as rectangular, that define apertures 934 therethrough configured to receive ring members 136 therein to secure extension assembly 940 to tab assembly 930. Extension assembly 940 includes a first extension 942 and a second extension 944. Each of the extensions 942, 944 includes an attachment end 946. Each attachment end 946 defines a recess 946a on an outer surface thereof and a threaded surface 946b on an inner surface thereof. A protuberance 946c extends from each recess 946a. Each protuberance 946c is receivable within one of the apertures 934 defined through the tabs 932 and the respective ring member 136 to secure the respective extension 142, 144 to the respective tab 932 similar to that described above with respect to rod reducer assembly 100. For example, the ring members 136 can be welded and/or friction fit to the protuberances 946c to secure the extensions 142, 144 to the respective tabs 932.

Turning now to FIGS. 25-28, a modular compressor 1000 can be used to manipulate a first rod reducer assembly 100a and a second rod reducer assembly 100b relative to another. The modular compressor 1000 includes a first leg 1010 and a second leg 1020 that are selectively couplable to one another by a fulcrum assembly 1030.

The first leg 1010 includes a handle 1012 that extends distally to a mounting arm 1014 disposed at an angle relative to the handle 1012. The mounting arm 1014 includes a mounting segment 1016 that extends distally from the handle 1012 and a coupling segment 1018 that extends distally from the mounting segment 1016. The mounting segment 1016 defines apertures 1016a, 1016b, 1016c therethrough and the coupling segment 1018 extends distally to a foot 1018a. The foot 1018a has an enclosed, circumferential shape that defines an opening 1018b configured to receive the head 110b of the pedicle screw 110 of the rod reducer assembly 100. The foot 1018a defines a transverse channel 1018c therethrough that is configured to receive a spinal rod, such as spinal rod "R," therethrough (see FIG. 1).

The second leg 1020 includes a handle 1022 that extends distally to a mounting arm 1024 disposed at an angle relative to the handle 1022. The mounting arm 1024 includes a mounting segment 1026 that extends distally from the handle 1022 and a coupling segment 1028 that extends distally from the mounting segment 1026. The mounting segment 1026 defines apertures 1026a, 1026b, 1026c therethrough and the coupling segment 1028 extends distally to a foot 1028a. The foot 1028a of the second leg 1020 includes an open, arcuate shape and is configured to receive the head 110b of the pedicle screw 110 of the rod reducer assembly 100. The foot 1028a defines a transverse channel 1028b configured to receive a spinal rod, such as spinal rod "R," therethrough (see FIG. 1).

The fulcrum assembly 1030 includes a first plate 1032 and a second plate 1034 that are selectively coupled to one another by a coupling pin 1036 and fasteners 1038a, 1038b. The first plate 1032 defines fastener holes 1032a, 1032b and a central pin hole 1032c. The second plate 1034 defines fastener holes 1034a, 1034b and a central pin hole 1034c. The fastener holes 1032a, 1032b of the first plate 1032 and the fastener holes 1034aa, 1034b of the second plate 1034 are configured to threadably receive the fasteners 1038a, 1038b to couple the first and second plates 1032, 1034 together about one of the mounting segments 1016, 1026 of the respective first and second legs 1010, 1020.

The coupling pin 1036 includes a base 1036a and a stem 1036b that extends from the base 1036a to a stem head 1036c. The coupling pin 1036 further defines a first groove 1036d in an outer surface thereof and proximal to the stem head 1036c, and a second groove 1036e about an outer surface of the stem head 1036c. The first and/or second grooves 1036d, 1036e may have an annular configuration. The first groove 1036d is configured to longitudinally align with the central pin hole 1034c of the second plate 1034 when the first and second plates 1032, 1034 are coupled to one of the first and second legs 1010, 1020. The second groove 1036e is configured to receive a fastening clip 1039 such as a C-clip, a cotter pin, or the like to prevent axial movement of the coupling pin 1036 relative to the first and second legs 101, 1020. The central pin holes 1032c, 1034c of the first and second plates 1032, 1034, respectively, are configured to align with one of the apertures 1016a-1016c, 1026a-1026c of the respective first or second legs 1010, 1020 for receiving the coupling pin 1036 therethrough such that the second groove 1036e can be positioned to receive the fastening clip 1039. Specifically, when the first and second legs 1010, 1020 are pivotally coupled together by the fulcrum assembly 1030, and the fastening clip 1039 is coupled to the second annular groove 1036e, the fastening clip 1039 is configured to prevent axial movement of the coupling pin 1036 to maintain the first and second legs 1010, 1020 pivotally coupled together by the fulcrum assembly 1030.

In use, with the fulcrum assembly 1030 coupled to one of the first or second legs 1010, 1020, the coupling pin 1036 is advanced through the central pin hole 1032c of the first plate 1032, one of the apertures 1016a-1016c, 1026a-1026c of the respective first or second legs 1010, 1020, and the central pin hole 1034c of the second plate 1034c. The stem head 1036c projects through the central pin hole 1034c of the second plate 1034c and is positioned to align with one of the apertures 1016a-1016c, 1026a-1026c of the other of the first and second legs 1010, 1020 for receipt therein to pivotally couple the first and second legs 1010, 1020 together as desired. The feet 1018a, 1028a of the respective first and second legs 1010, 1020 can be separately attached to one of the first or second rod reducer assemblies 100a, 100b. Once each of the first and second legs 1010, 1020 are coupled to a respective one of the first or second rod reducer assemblies 100a, 100b, the first and second legs 1010, 1020 are pivotally coupled together by positioning the stem head 1036c of the coupling pin 1036 through one of the respective apertures 1016a-1016c, 1026a-1026c of the opposing one of the first and second legs 1010, 1020. Once the first and second legs 1010, 1020 are pivotally coupled about the coupling pin 1036, the fastening clip 1039 can be secured to the stem head 1036c as detailed above to axial fix the position of the coupling pin 1036 and maintain the first and second legs 1010, 1020 pivotally coupled together.

Figure 27:
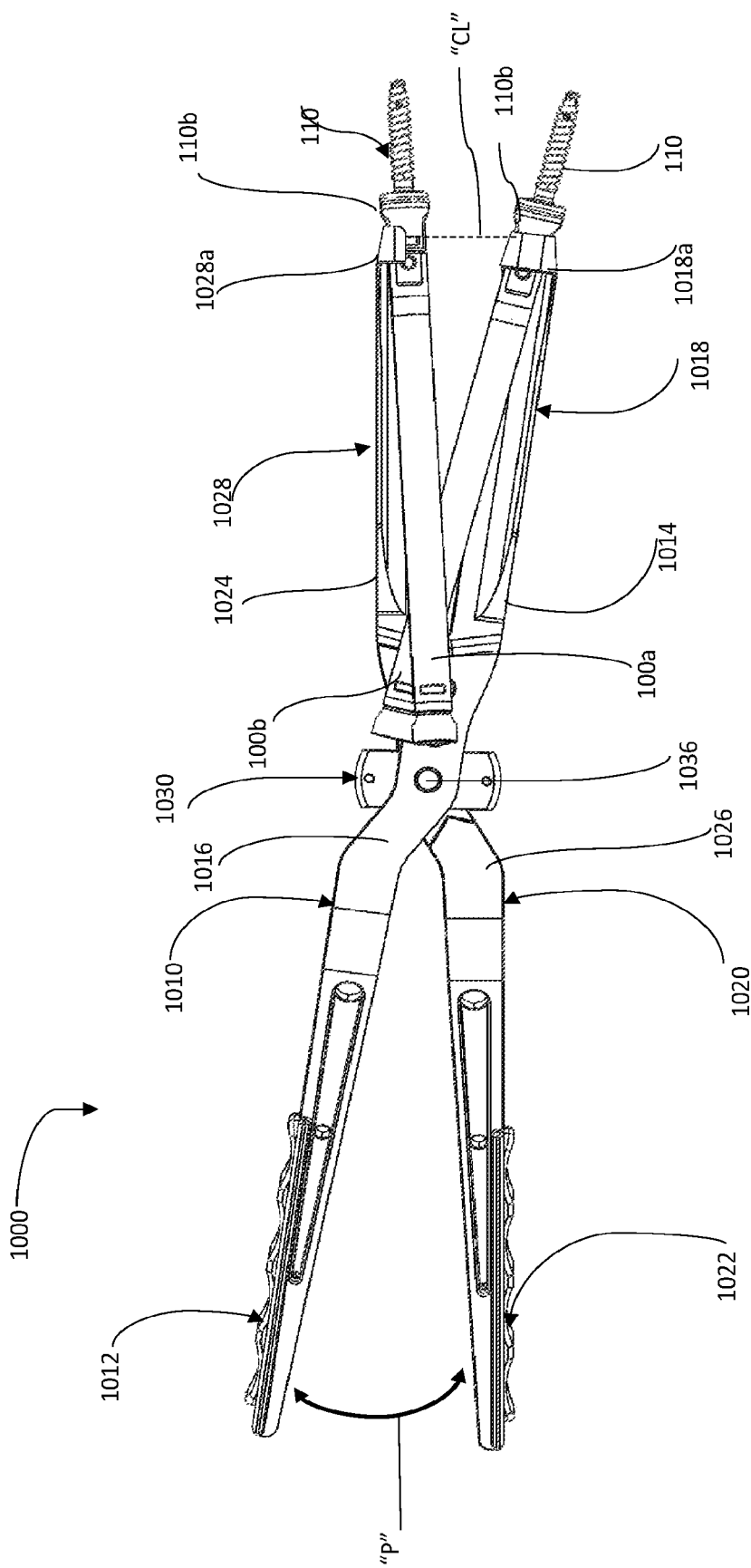
FIGS. 27 and 28 are front and side views, respectively, illustrating the modular compressor attached to two rod reducer assemblies.
Figure 28:
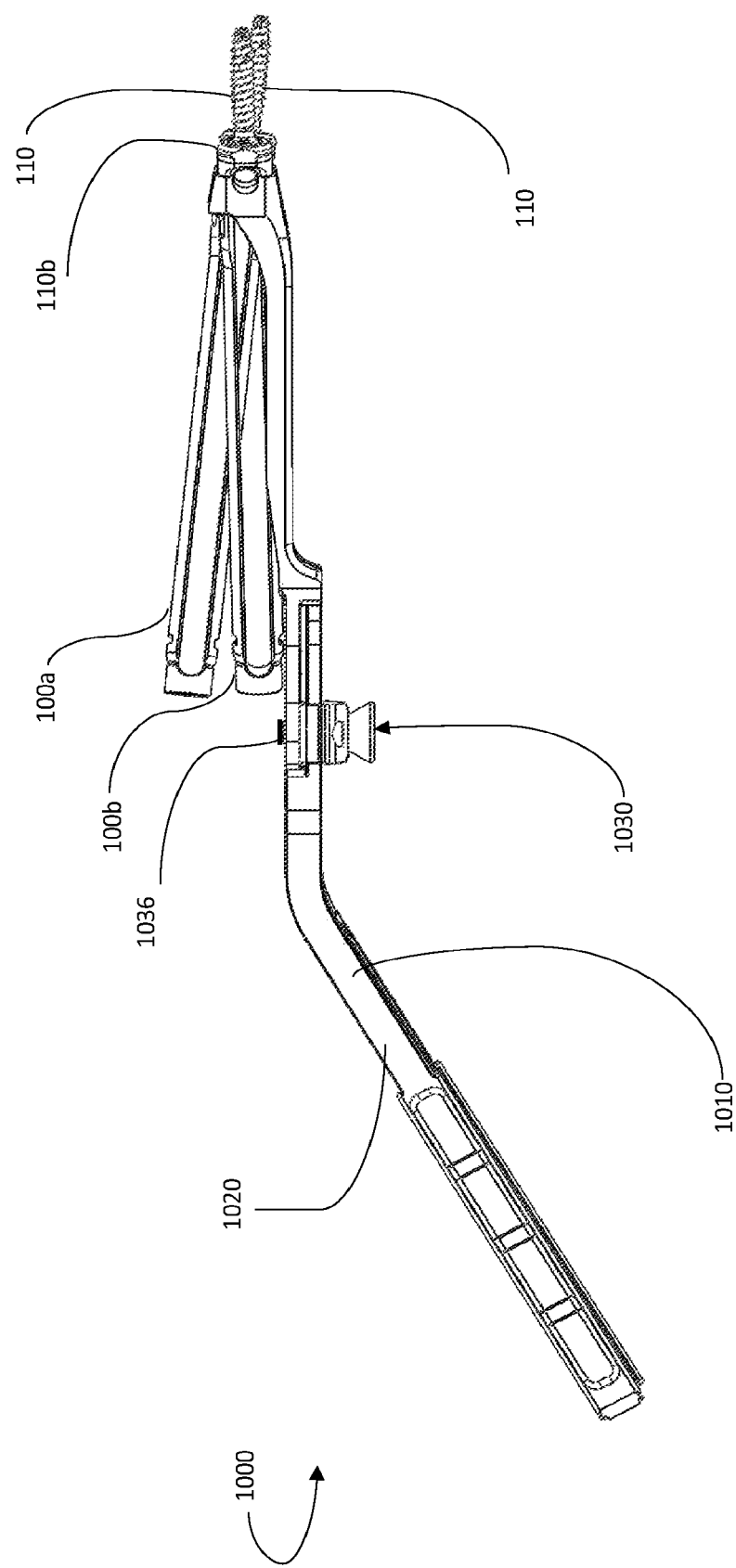

Once the first and second legs 1010, 1020 are fixedly pivotally coupled together by the coupling pin 1036 and the fastening clip 1039 of the fulcrum assembly 1030, the handles 1012, 1022 of the respective first and second legs 1010, 1020 can be pivoted toward or away from one another, as indicated by arrows "P," to manipulate the first and second rod reducer assemblies 100a, 100b relative to one another while mounted to bone (FIG. 27). The feet 1018a, 1028a of the respective first and second legs 1010, 1020 are configured to enable up to at least 10 degrees of angulation of the heads 110b of the pedicle screws 110 of the respective rod reducer assemblies 100a, 100b while pushing along a spinal rod centerline "CL" as the first and second rod reducer assemblies 100a, 100b approximate and/or cross one another in response to compressive pivoting movement of the modular compressor 1000 (see FIGS. 27 and 28).

Any of the presently disclosed embodiments, or components thereof, can be formed of any suitable material or combinations of materials. For example, one or more of the presently described rod reducer assemblies 100, 800, and/or 900, and/or one or more components thereof, can include mixed metallic materials such as titanium alloy and cobalt-chromium. In one instance, the extension assemblies 140, 940 and the rings 136 can include titanium alloy while the pedicle screw housings 120 and tab assemblies 130, 930 can include cobalt-chromium.

Any of the presently disclosed embodiments, or components thereof can be formed using any suitable technique such as welding, fastening, machining, molding, etc. In some embodiments, one or more of the components can be secured together using any suitable technique such as welding, fastening, machining, molding, etc.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A method for manipulating vertebrae of a spine, comprising:
coupling a first leg of a compressor to a first rod reducer assembly;
coupling a second leg of the compressor to a second rod reducer assembly;
pivotally coupling together the first and second legs of the compressor by a fulcrum, such that the first and second legs of the compressor are secured to each other by the fulcrum while being pivotable with respect to one another about a pivot axis defined by the fulcrum; and
pivoting the first and second legs relative to one another about the pivot axis to manipulate the first and second rod reducer assemblies relative to one another.

2. The method of claim 1, wherein the step of pivotally coupling together the first and second legs of the compressor occurs after the steps of coupling the first and second legs to the respective first and second rod reducer assemblies.

3. The method of claim 1, wherein the step of pivotally coupling together the first and second legs of the compressor includes positioning a coupling pin of the fulcrum into one of a plurality of first apertures defined along a portion of the first leg.

4. The method of claim 3, wherein the coupling pin extends through one of a plurality of second apertures defined along a portion of the second leg.

5. The method of claim 3, wherein the fulcrum is coupled to the second leg before the steps of coupling the first and second legs to the respective first and second rod reducer assemblies and before the step of pivotally coupling together the first and second legs.

6. The method of claim 1, wherein the step of coupling the first leg of the compressor to the first rod reducer assembly includes receiving at least a portion of the first rod reducer assembly through an enclosed opening defined by a distal portion of the first leg.

7. The method of claim 1, wherein the step of coupling the second leg of the compressor to the second rod reducer assembly includes receiving at least a portion of the second rod reducer assembly within an open concave segment defined by a distal portion of the second leg.

8. The method of claim 1, wherein the first rod reducer assembly is monolithically formed with a housing of a pedicle screw that is anchored to a vertebral bone.

9. The method of claim 8, wherein the first rod reducer assembly is coupled to the housing of the pedicle screw via a frangible connection configured to break upon application of a threshold force to the frangible connection.

10. The method of claim 1, wherein the step of pivoting the first and second legs relative to one another includes grasping a first handle of the first leg and a second handle of the second leg, each of the first and second handles extending at an oblique orientation relative to a respective first and second longitudinal mounting arm of the respective first and second leg.

11. The method of claim 1, wherein the step of coupling the second leg to the second rod reducer assembly includes receiving at least a portion of the second rod reducer assembly within an open concave segment defined by a distal portion of the second leg.

12. A method for manipulating vertebrae of a spine, comprising:
   selecting a selected fulcrum location from among a plurality of possible fulcrum locations along a first leg of a compressor;
   pivotally coupling the first leg of the compressor to a second leg of the compressor by a fulcrum positioned at the selected fulcrum location, such that the first and second legs of the compressor are secured to each other by the fulcrum while being pivotable with respect to one another about a pivot axis defined by the fulcrum and extending through the selected fulcrum location;
   engaging a coupling portion of each of the first and second legs of the compressor to a respective first and second pedicle fastener anchored to a respective first and second vertebra; and
   pivoting the first and second legs relative to one another about the pivot axis at the fulcrum location to induce a compression force on each of the first and second pedicle fasteners directed towards the other of the first and second pedicle fasteners.

13. The method of claim 12, further comprising selecting a selected second fulcrum location from among a plurality of possible second fulcrum locations along the second leg of the compressor; wherein the step of pivotally coupling the first leg to the second leg comprises pivotally coupling the selected fulcrum location of the first leg to the selected second fulcrum location of the second leg by the fulcrum.

14. The method of claim 13, wherein the step of selecting the selected second fulcrum location occurs before the step of engaging the coupling portion of each of the first and second legs to the respective first and second pedicle fasteners.

15. The method of claim 12, wherein the step of pivotally coupling the first leg to the second leg occurs after the step of engaging the coupling portion of each of the first and second legs to the respective first and second pedicle fasteners.

16. The method of claim 12, wherein the step of pivotally coupling the first leg to the second leg includes positioning a coupling pin of the fulcrum into one of a plurality of first apertures defined along a portion of the first leg.

17. The method of claim 12, wherein the step of coupling the first leg to the first rod reducer assembly includes receiving at least a portion of the first rod reducer assembly through an enclosed opening defined by a distal portion of the first leg.

18. The method of claim 12, wherein the first pedicle fastener includes a rod reducer assembly coupled thereto during the steps of engaging the coupling portion of each of the first and second legs to the respective first and second pedicle fasteners and pivoting the first and second legs relative to one another.

19. The method of claim 12, wherein the step of pivoting the first and second legs relative to one another includes grasping a first handle of the first leg and a second handle of the second leg, each of the first and second handles extending at an oblique orientation relative to a respective first and second longitudinal mounting arm of the respective first and second leg.

20. A method for manipulating vertebrae of a spine, comprising:
   selecting a selected fulcrum location from among a plurality of possible fulcrum locations along a first leg of a compressor;
   selecting a selected second fulcrum location from among a plurality of possible second fulcrum locations along a second leg of the compressor;
   pivotally coupling the selected fulcrum location of the first leg of the compressor to the selected second fulcrum location of the second leg of the compressor;
   engaging a coupling portion of each of the first and second legs of the compressor to a respective first and second pedicle fastener anchored to a respective first and second vertebra; and pivoting the first and second legs relative to one another about the fulcrum location to induce a compression force on each of the first and second pedicle fasteners directed towards the other of the first and second pedicle fasteners.

\* \* \* \* \*